(12) United States Patent
Suzuki et al.

(10) Patent No.: US 7,807,777 B2
(45) Date of Patent: Oct. 5, 2010

(54) MARKER PEPTIDE FOR ALZHEIMER'S DISEASE

(75) Inventors: Toshiharu Suzuki, Chiba (JP); Yoichi Araki, Sapporo (JP); Naomi Miyagi, Sapporo (JP); Haruyasu Yamaguchi, Maebashi (JP); Masaki Nishimura, Kusatsu (JP); Kazuo Yamamoto, Tokyo (JP)

(73) Assignee: Immuno-Biological Laboratories Co., Ltd., Fujioka-shi (JP)

( * ) Notice: Subject to any disclaimer, the term of this patent is extended or adjusted under 35 U.S.C. 154(b) by 58 days.

(21) Appl. No.: 10/577,008

(22) PCT Filed: Nov. 1, 2004

(86) PCT No.: PCT/JP2004/016209

§ 371 (c)(1),
(2), (4) Date: Aug. 7, 2006

(87) PCT Pub. No.: WO2005/044847

PCT Pub. Date: May 19, 2005

(65) Prior Publication Data

US 2007/0111252 A1    May 17, 2007

(30) Foreign Application Priority Data

Nov. 5, 2003    (JP) .............................. 2003-375363

(51) Int. Cl.
*A61K 38/00*    (2006.01)
*A61K 38/04*    (2006.01)
*C07K 16/00*    (2006.01)
*G01N 33/53*    (2006.01)
*G01N 33/542*    (2006.01)

(52) U.S. Cl. ........................ 530/300; 530/324; 530/326; 435/7.1; 435/7.9; 435/7.92

(58) Field of Classification Search ....................... None
See application file for complete search history.

(56) References Cited

FOREIGN PATENT DOCUMENTS

| JP | 2003-164298 A | 6/2003 |
|----|---------------|--------|
| WO | WO-02/22819 A1 | 3/2002 |
| WO | WO-02/22819 A2 | 3/2002 |

OTHER PUBLICATIONS

Yoichi Araki et al.; The Journal of Biological Chemistry, vol. 278, No. 49, pp. 49448-49458, Dec. 5, 2003.
Yoichi Araki et al.; The Journal of Biological Chemistry, vol. 279, No. 23, pp. 24343-24354, Jun. 4, 2004.
Vogt, Lorenz et al.; Molecular and Cellular Neurosciences, vol. 17, pp. 151-166 (2001).

*Primary Examiner*—Olga N Chernyshev
(74) *Attorney, Agent, or Firm*—Birch, Stewart, Kolasch & Birch, LLP.

(57) ABSTRACT

To provide a peptide obtainable by cleaving an N-terminal region and a C-terminal region of Alcadein α, Alcadein β, or Alcadein γ; and capable of being a diagnostic marker for Alzheimer's disease. It is possible to detect Alzheimer's disease at an early stage without burdening subjects to be tested by using the peptide as a diagnostic marker.

2 Claims, 22 Drawing Sheets

1   Alc α          2   APP          3   Control

MARKER PEPTIDE FOR ALZHEIMER'S DISEASE

TECHNICAL FIELD

The present invention relates to peptides which can be used as diagnostic markers for Alzheimer's disease, methods for diagnosing Alzheimer's disease using the peptides, methods for collecting data for diagnosing Alzheimer's disease by using the peptides, methods for screening for therapeutic agents for Alzheimer's disease by using the peptides, antibodies to the peptides, and diagnostic reagents including the antibodies.

BACKGROUND ART

Alzheimer's disease is currently diagnosed by carrying out an interview with a specialized physician and evaluating the degree of brain atrophy using MRI or the like. However, it is difficult to obtain an objective and correct diagnostic conclusion by interview only. Furthermore, it is impossible to identify a so-called pre-patient, before the onset of symptoms. Additionally, apparatuses such as MRI apparatuses are expensive and consequently can be used only in large special hospitals.

Under such circumstances, biochemical diagnosis using a marker is adopted as a simple and objective method. Among main markers for Alzheimer's disease, intracellular tau protein and β-amyloid (hereinafter referred to as "Aβ") are known at present (Non-Patent Document 1 and Non-Patent Document 2).

Tau protein is a component constituting microtubules in nerve cells and is leaked out from the cells when the nerve cells are degenerated during an Alzheimer's disease process. As a result, tau protein is detected in cerebrospinal fluid, and is a useful marker. However, tau protein cannot be detected until the condition of the disease progresses. Furthermore, since the leakage amount is small, tau protein is hardly detected in body fluid (for example, blood) other than the cerebrospinal fluid.

Aβ is a causative substance of Alzheimer's disease. Therefore, Aβ can be a most effective marker provided that a quantitative change (an increase in the production) or a qualitative change (an increase in the ratio of highly aggregative Aβ can be precisely measured. However, since Aβ shows aggregative nature, the amount of Aβ detected in a patient's cerebrospinal fluid is rather lower than that of healthy subjects.

Non-Patent Document 1: "Decreased beta-amyloid 1-42 and increased tau levels in cerebrospinal fluid of patients with Alzheimer disease"; Sunderland, T., Linker, G., Mirza, N., Putnam, K. T., Friedman, D. L., Kimmel, L. H., Bergeson, J., Manetti, G. J., Zimmermann, M., Tang, B., Bartko, J. J., and Cohen, R. M. JAMA 2003, 289, 2094-2103.

Non-Patent Document 2: "Cerebrospinal fluid biomarkers for disease stage and intensity in cognitively impaired patients"; Wahlund, L. O., and Blennow, K. Neurosci. Lett. 2003, 339, 99-102.

DISCLOSURE OF INVENTION

Problems to be Solved by the Invention

As mentioned above, it is difficult to detect Alzheimer's disease at an early stage by a diagnostic method using currently known markers. Furthermore, it is also difficult to diagnose Alzheimer's disease by a method such as blood examination, which is less of a burden on patients.

The present invention has been accomplished under the above-mentioned technical background, and it is an object of the present invention to provide a method for easily and accurately diagnosing Alzheimer's disease.

MEANS FOR SOLVING THE PROBLEM

The present inventors have performed intensive studies in order to solve the above-mentioned problems and, as a result, have found that Alcadein, which is a protein, is cleaved by an enzyme that cleaves a precursor protein of Aβ (hereinafter referred to as "APP") and then is extracellularly secreted in the same manner as in Aβ. It has been already reported that Alcadein forms a triple complex with X11L and APP and the formation of the complex suppresses the production of Aβ (Araki, Y. et al., J. Biol. Chem. 2003, 278, 49448-49458 and Japanese Unexamined Patent Application Publication No. 2003-164298). However, the fact that Alcadein is cleaved by the enzyme which cleaves APP and is extracellularly secreted in the same manner as in Aβ is a completely new finding. Additionally, the present inventors have found that the amount of a high-molecular-weight peptide generated from Alcadein by its consecutive cleavages is increased under the conditions that the amount of a high-molecular-weight Aβ, which is highly aggregative and highly neurotoxic, is increased.

The present invention has been accomplished on the basis of the foregoing findings.

Accordingly, the present invention provides the following aspects (1) to (15):

(1) a peptide obtainable by cleaving an N-terminal region and a C-terminal region of Alcadein α, Alcadein β, or Alcadein γ; and capable of being a diagnostic marker for Alzheimer's disease (hereinafter the peptide is simply referred to as "peptide of the present invention");

(2) the peptide according to the aspect (1), wherein the N-terminal region to be cleaved is a portion of an extracellular domain at the N-terminal;

(3) the peptide according to the aspect (1) or (2), wherein the C-terminal region is cleaved by presenilin);

(4) the peptide according to the aspect (1), wherein the peptide is obtained by cleaving an N-terminal region and a C-terminal region of Alcadein α; and the cleavage site of the N-terminal region is between amino acids 815 and 816, amino acids 820 and 821, or amino acids 838 and 839 of the amino acid sequence represented by SEQ ID NO: 1;

(5) the peptide according to the aspect (1) or (2), wherein the peptide is obtained by cleaving an N-terminal region and a C-terminal region of Alcadein α; and the cleavage site of the C-terminal region is between amino acids 842 and 843, amino acids 843 and 844, or amino acids 851 and 852 of the amino acid sequence represented by SEQ ID NO: 1;

(6) the peptide according to the aspect (1), consisting of an amino acid sequence represented by any one of SEQ ID NOS: 4 to 12;

(7) a method for collecting data for diagnosing Alzheimer's disease, including a process of detecting or quantitatively determining the peptide according to any one of the aspects (1) to (6) in body fluid or tissues taken from an animal;

(8) the method for collecting data for diagnosing Alzheimer's disease according to the aspect (7), wherein the body fluid is blood or cerebrospinal fluid;

(9) the method for collecting data for diagnosing Alzheimer's disease according to aspect (7) or (8), wherein a ratio of a high-molecular-weight peptide in the detected or quantitatively determined peptide is used as an indicator for diagnosing Alzheimer's disease;

(10) a method for diagnosing Alzheimer's disease, including a process of detecting or quantitatively determining the peptide according to any one of the aspects (1) to (6) in body fluid or tissues taken from an animal;

(11) the method for diagnosing Alzheimer's disease according to the aspect (10), wherein the body fluid is blood or cerebrospinal fluid;

(12) the method for diagnosing Alzheimer's disease according to the aspect (10) or (11), wherein a ratio of a high-molecular-weight peptide in the detected or quantitatively determined peptide is used as an indicator for diagnosing Alzheimer's disease;

(13) a method for screening a therapeutic agent for Alzheimer's disease by contacting cells secreting the peptide according to any one of the aspects (1) to (6) with an agent to be screened and determining a change in the secreted amount of the peptide or a change in the molecular species of the secreted peptide;

(14) an antibody against the peptide according to any one of the aspects (1) to (6); and

(15) a diagnostic reagent for Alzheimer's disease, including the antibody according to the aspect (14).

Advantageous Effect Of The Invention

By utilizing the peptide of the present invention, Alzheimer's disease can be detected before clinical symptoms or at an early stage by a simple method which does not put a burden on subjects to be tested.

BEST MODE FOR CARRYING OUT THE INVENTION

Figure 1:
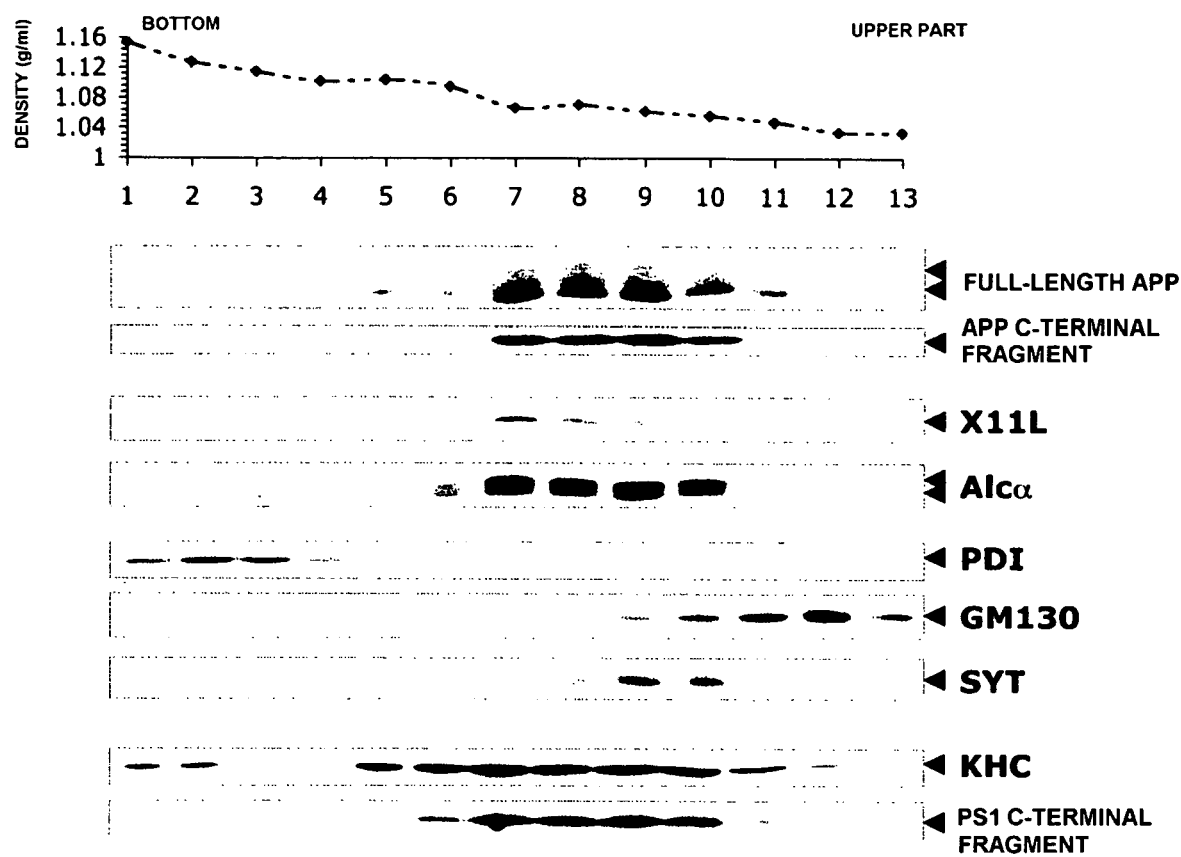
FIG. 1 is a photograph showing the results of Western blotting of proteins separated by density-gradient centrifugation.

The present invention will now be described in detail.

The peptide of the present invention is obtained by cleaving at N-terminal and C-terminal regions of Alcadein α, Alcadein β, or Alcadein γ. The peptide generated by these cleavages can be a diagnostic marker for Alzheimer's disease.

There are three types of Alcadein: Alcadein α (hereinafter referred to as "Alcα"), Alcadein β (hereinafter referred to as "Alcβ"), and Alcadein γ (hereinafter referred to as "Alcγ"). Alcα is a protein including an amino acid sequence which is the same or substantially the same as the amino acid sequence represented by SEQ ID NO: 1, Alcβ is a protein including an amino acid sequence which is the same or substantially the same as the amino acid sequence represented by SEQ ID NO: 2, and Alcγ is a protein including an amino acid sequence which is the same or substantially the same as the amino acid sequence represented by SEQ ID NO: 3.

Alcα, Alcβ, and Alcγ may be proteins derived from any kind of cell (for example, hepatocytes, splenocytes, neurons, glia cells, pancreatic β-cells, myelocytes, mesangial cells, Langerhan's cells, epidermal cells, epithelial cells, goblet cells, endothelial cells, smooth muscle cells, fibroblasts, fibrous cells, muscle cells, fat cells, immune cells (e.g., macrophages, T-cells, B-cells, natural killer cells, mast cells, neutrophils, basophils, eosinophils, and monocytes), megakaryocytes, synovial cells, chondrocytes, osteocytes, osteoblasts, osteoclasts, mammary cells, hepatocytes, interstitial cells, progenitor cells of these cells, stem cells, and cancer cells) of human and warm-blooded animals (for example, guinea pig, rat, mouse, chicken, rabbit, swine, sheep, bovine, and monkey) or all tissues in which such cells are present, such as brain, various parts of brain (e.g., olfactory bulb, amygdaloid nucleus, cerebral basal nucleus, hippocampus, thalamus, hypothalamus, cerebral cortex, medulla oblongata, and cerebellum), spinal cord, pituitary gland, stomach, pancreas, kidney, liver, gonad, thyroid, gall-bladder, bone marrow, adrenal gland, skin, muscle, lung, gastrointestinal tract (e.g., large intestine and small intestine), blood vessels, heart, thymus, spleen, submandibular gland, peripheral blood, prostate, testis, ovary, placenta, uterus, bone, joint, and skeletal muscle, and furthermore, may be synthetic proteins as well.

Examples of the amino acid sequence which is substantially the same as the amino acid sequence represented by SEQ ID NO: 1, SEQ ID NO: 2, or SEQ ID NO: 3 include amino acid sequences which contain not less than about 50%, preferably not less than about 60%, more preferably not less than about 70%, still more preferably not less than about 80%, furthermore preferably not less than about 90%, most preferably not less than about 95% identity to the amino acid sequence represented by SEQ ID NO: 1, SEQ ID NO: 2, or SEQ ID NO: 3, respectively. Preferable examples of the protein which includes an amino acid sequence substantially the same as the amino acid sequence represented by SEQ ID NO: 1, SEQ ID NO: 2, or SEQ ID NO: 3 are proteins having the amino acid sequence substantially the same as the amino acid sequence represented by SEQ ID NO: 1, SEQ ID NO: 2, or SEQ ID NO: 3 and having an activity of substantially the same quality as that of the protein including the amino acid sequence represented by SEQ ID NO: 1, SEQ ID NO: 2, or SEQ ID NO: 3.

An example of the activity which has substantially the same quality as that of a protein is an activity that binds with the PI domain of X11L. The term substantially the same quality means the natures are equivalent (for example, physiologically or pharmacologically). Therefore, it is preferable that the above-mentioned activities are equivalent (e.g., about 0.01 to 100 times, preferably about 0.1 to 10 times, more preferably about 0.5 to 2 times), but it is allowable that the degrees of the activities and the quantitative elements such as molecular weight of the proteins are at different levels.

Alcα, Alcβ, and Alcγ of the present invention each include, for example, so-called muteins such as proteins including (1) an amino acid sequence wherein one or more amino acids (preferably about 1 to 30, more preferably about 1 to 10, and further preferably a few (1 to 5) amino acids) are deleted from the amino acid sequence represented by SEQ ID NO: 1, SEQ ID NO: 2, or SEQ ID NO: 3, (2) an amino acid sequence wherein one or more amino acids (preferably about 1 to 30, more preferably about 1 to 10, and further preferably a few (1 to 5) amino acids) are added to the amino acid sequence represented by SEQ ID NO: 1, SEQ ID NO: 2, or SEQ ID NO: 3, (3) an amino acid sequence wherein one or more amino acids (preferably about 1 to 30, more preferably about 1 to 10, and further preferably a few (1 to 5) amino acids) are inserted into the amino acid sequence represented by SEQ ID NO: 1, SEQ ID NO: 2, or SEQ ID NO: 3, (4) an amino acid sequence wherein one or more amino acids (preferably about 1 to 30, more preferably about 1 to 10, and further preferably a few (1 to 5) amino acids) in the amino acid sequence represented by SEQ ID NO: 1, SEQ ID NO: 2, or SEQ ID NO: 3 are substituted with other amino acids, or (5) a combination thereof. When an amino acid sequence has the above-mentioned insertion, deletion, or substitution, the site of the insertion, deletion, or substitution is not limited as long as the activity is maintained. Specifically, as regards Alcadein α, Alcadein α1 having the amino acid sequence represented by SEQ ID NO: 1 and Alcadein α2 having an amino acid sequence wherein 10 amino acids are inserted between amino acids 71 and 72 of the amino acid sequence represented by SEQ ID NO: 1 are known.

The site where an N-terminal region is cleaved is not limited as long as the obtained peptide can be a diagnostic marker for Alzheimer's disease, but it is preferable that the site is within an extracellular domain at the N-terminal side. Generally, such a site is, in the case of Alcα, between amino acids 815 and 816, amino acids 820 and 821, or amino acids 838 and 839 of the amino acid sequence represented by SEQ ID NO: 1 or in the vicinities thereof; in the case of Alcα, between amino acid 825 and 826 of the amino acid sequence represented by SEQ ID NO: 2 or in the vicinity thereof; and in the case of Alcγ, between amino acids 804 and 805 of the amino acid sequence represented by SEQ ID NO: 3 or in the vicinity thereof.

Furthermore, Alcadein is cleaved at another site at the N-terminal side too in the same manner as in APP: Alcα is also cleaved extracellularly by BACE which cleaves APP at the β-site. Generally, such a site is between amino acid 708 and 709 of the amino acid sequence represented by SEQ ID NO: 1 or in the vicinity thereof.

The site where a C-terminal region is cleaved is not limited as long as the obtained peptide can be a diagnostic marker for Alzheimer's disease, but it is preferably that the site is cleaved by presenilin. Generally, such a site is, in the case of Alcα, between amino acids 842 and 843, amino acids 843 and 844, or amino acids 851 and 852 of the amino acid sequence represented by SEQ ID NO: 1 or in the vicinities thereof; in the case of Alcβ, between amino acids 875 and 876 of the amino acid sequence represented by SEQ ID NO: 2 or in the vicinity thereof; and in the case of Alcγ, between amino acids 847 and 848 of the amino acid sequence represented by SEQ ID NO: 3 or in the vicinity thereof. Here, the term "vicinity" means generally a range within 10 amino acids, preferably a range within 5 amino acids from the cleavage site. Specific examples of the peptide of the present invention include a peptide consisting of an amino acid sequence represented by any one of SEQ ID NOS: 4 to 12.

It is thought that the peptide of the present invention can be used as a diagnostic marker for Alzheimer's disease because of the following reasons:

(1) the peptide of the present invention is obtained from Alcadein that forms a triple complex with APP and X11L (Araki, Y. et al., J. Biol. Chem. 2003, 278, 49448-49458 and Japanese Unexamined Patent Application Publication No. 2003-164298) and is distributed in the brain of an Alzheimer's disease patient in the same manner as in APP (Examples 2 and 3);

(2) Alcadein is cleaved by BACE as in APP (Example 8);

(3) the peptide of the present invention is obtained by the cleavage by presenilin as in Aβ (Examples 4, 6, and 7) and further secreted extracellularly as in Aβ (Example 7), and when the molecular species of Aβ is pathologically changed, the molecular species of the peptide of the present invention is also similarly changed (Example 11). On the basis of these facts, it is thought that the generation amount of Aβ can be predicted from the generation amount of the peptide of the present invention and that the qualitative change of Aβ can be predicted from the qualitative change of the peptide of the present invention; and (4) Aβ cannot be used as a quantitative diagnostic marker for Alzheimer's disease because of its aggregative ability. Aβ has an α-helix structure at the N-terminal side and a β-sheet structure at the C-terminal side, and a sequence composed of the 26th to the 29th amino acids forms a β-turn structure at the central portion. Consequently, an antiparallel β-sheet structure is formed by the N-terminal side and the C-terminal side. It is understood that this causes the aggregation of Aβ ("Oligomerization and fibril assembly of the amyloid β-protein" by Roher, A. E., et al., Biochem. Boiphy. Act 2000, 1502, 31-43). On the other hand, though the peptide of the present invention has an α-helix structure at the N-terminal side and a β-sheet structure at the C-terminal side as in the basic structure of Aβ, the peptide does not have a sequence to form a β-turn structure. Therefore, it is thought that since it is predicted that the α-helix structure is not converted to a β-sheet structure, the peptide does not have aggregative ability.

By using the peptide of the present invention as a diagnostic marker for Alzheimer's disease, Alzheimer's disease can be diagnosed and data for the diagnosis can be collected. Specifically, the diagnosis and the collection of data can be performed by detecting or quantitatively determining the peptide of the present invention in body fluid or tissues taken from animals.

The peptide of the present invention is available in various molecular weights. When a large amount of high-molecular-weight peptide is contained in the peptide of the present invention to be detected or quantitatively determined, it suggests a high possibility of Alzheimer's disease or its pre-stage. This is based on the fact that the amount of the high-molecular-weight peptide of the present invention is increased under the conditions that the amount of a high-molecular-weight Aβ (Aβ42), which is highly aggregative and highly toxic, is increased (Examples 11 and 12). Therefore, Alzheimer's disease can be diagnosed by using the ratio of the amount of high-molecular-weight peptide to the total amount of the peptide of the present invention as an indicator, in addition to the determination of whether a certain amount of the peptide of the present invention is present in body fluid or the like. Here, the term "high-molecular-weight peptide" means a peptide which is obtained when the cleavage site of an N-terminal region is closer to the N-terminal end, or the cleavage site of a C-terminal region is closer to the C-terminal end, or a combination of both. For example, the high-molecular-weight peptide is defined as a molecular species which is obtained when the cleavage site is shifted to the N-terminal end, the C-terminal end, or both ends from the site of each of the β-Alc molecular species shown in Table 1 described below. Thus, the high-molecular-weight peptide is not specifically defined by its molecular weight. When a primary cleavage site is ζ1 and a secondary cleavage site is γ3 as shown in Table 1, it is predicted that a peptide composed of 36 amino acids and having a molecular weight of about 4000 is obtained. If β-Alc has a molecular weight higher than that of this peptide by the shift of the cleavage site to the N-terminal end or the C-terminal end, the β-Alc is categorized as the above-mentioned "high-molecular-weight peptide". When a primary cleavage site is ζ3 and a secondary cleavage site is γ1 as shown in Table 1, it is predicted that a peptide composed of 4 amino acids and having a molecular weight of 500 to 600 is obtained. If β-Alc has a molecular weight higher than that of this peptide by the shift of the cleavage site to the N-terminal end or the C-terminal end, the β-Alc is categorized as the above-mentioned "high-molecular-weight peptide" even if the molecular weight is about 1000.

Examples of the animal from which body fluid or the like is taken include not only human but also warm-blooded animals other than human such as guinea pig, rat, mouse, chicken, rabbit, swine, sheep, bovine, and monkey.

Examples of the body fluid and tissues include blood, plasma, serum, cerebrospinal fluid, and brain tissues. Among them, blood and cerebrospinal fluid are preferable.

The method for detecting or quantitatively determining the peptide is not limited. Examples of the method include methods using an antibody, e.g., Western blotting, dot blotting, ELISA, sandwich ELISA, radioimmunoassay, and immunoprecipitation; mass spectrometry using a MALDI-TOF/MS; and combinations thereof. Among them, sandwich ELISA is most preferable. The sandwich ELISA may be conducted according to the description in the document of Tomita, et al. ("Cleavage of Alzheimer's amyloid precursor protein (APP) by secretases occurs after O-glycosylation of APP in the protein secretory pathway" Tomita, S., Kirino, Y., and Suzuki, T. J. Biol. Chem. 1998, 273, 6277-6284), for example. Specifically, the peptide of the present invention in a sample solution can be detected or quantitatively determined by (1) immobilizing an antibody specific to the peptide of the present invention on a solid phase, (2) adding the sample solution to the solid phase, (3) washing the solid phase, (4) adding another antibody specific to the peptide of the present invention, (5) adding an enzyme-labeled antibody (anti-IgG antibody) against the antibody, and (6) adding a substrate specific for the enzyme to detect the coloring or the like as an indicator. Here, the antibody specific to the peptide of the present invention can be prepared by a method described below. The anti-IgG antibody which is commercially available may be used. Examples of the solid phase include a micro-titer well and latex particles. Examples of the enzyme label include horseradish peroxidase, alkali phosphatase, and galactosidase.

The antibody of the present invention may be a monoclonal antibody or a polyclonal antibody.

The monoclonal antibody can be prepared, for example, by the method disclosed in the above-mentioned document of Tomita, et al. Specifically, a desired monoclonal antibody can be prepared by (1) administering the peptide of the present invention to an animal, (2) isolating antibody-producing cells from the animal, (3) fusing the antibody-producing cells with myeloma cells to prepare hybridomas, (4) selecting a hybridoma producing an antibody of the present invention from the hybridomas, and (5) separating and purifying the antibody from the culture supernatant of the antibody-producing hybridoma.

The peptide of the present invention to be administered to an animal may be the whole peptide or a partial peptide thereof. The partial peptide to be administered is not limited, but it is preferable that, in the case of a peptide derived from Alcα, the peptide has the amino acid at position 816, 821, or 839 of the amino acid sequence represented by SEQ ID NO: 1 as the N-terminal end and the amino acid at position 842, 843, or 851 of the amino acid sequence represented by SEQ ID NO: 1 as the C-terminal end; in the case of a peptide derived from Alcβ, the peptide is composed of the amino acids at positions 826 to 845 of the amino acid sequence represented by SEQ ID NO: 2; and in the case of a peptide derived from Alcγ, the peptide is composed of the amino acids at positions 805 to 824 of the amino acid sequence represented by SEQ ID NO: 3. In addition, the peptide may be administered with a complete or incomplete Freund's adjuvant in order to enhance the antibody productivity. The Animal to be administered with the peptide is not limited. For example, monkey, rabbit, dog, guinea pig, mouse, rat, sheep, goat, and chicken may be used. The peptide administration intervals and number of times are not limited. In general, the peptide is administered about 2 to 10 times for every 2 to 6 weeks. The antibody-producing cells can be obtained by extracting spleen cells or lymph nodes from the animal 2 to 5 days after the last immunization. The myeloma cells to be used are not limited. For example, NS-1, P3U1, SP2/0, or AP-1 may be used. The hybridization can be performed by a general method using a polyethylene glycol or Sendai virus. The selection of a hybridoma which produces the antibody of the present invention can be performed, for example, by applying a culture supernatant of hybridomas to a micro-plate on which the peptide of the present invention is adsorbed, adding an anti-IgG antibody labeled with an enzyme, and detecting the anti-IgG antibody bound to the micro-plate. The isolation of the antibody of the present invention from the hybridoma culture supernatant can be performed by a general method for isolating and purifying immunoglobulin, e.g., salting-out, alcohol precipitation, isoelectric precipitation, electrophoresis, adsorption and desorption by an ion-exchanger, ultracentrifugation, or gel-filtration.

The polyclonal antibody can be also prepared, for example, according to the method disclosed in the documents of Araki, et al. (Araki, Y., et al., J. Biol. Chem. 2003, 278, 49448-49458 and Araki, Y., et al., J. Biol. Chem. 2004, 279, 24343-24354). Specifically, a desired polyclonal antibody can be prepared by (1) administering the peptide of the present invention to an animal, (2) extracting blood or ascites fluid from the animal, and (3) isolating and purifying the antibody from the blood or the like. The administration of the peptide and the isolation and purification of the antibody can be performed by the same manner as in the monoclonal antibody.

A diagnostic reagent of the present invention is generally prepared by adding the above-mentioned antibody of the present invention to an appropriate buffer solution. The concentration of the antibody and the kind of the buffer solution are not limited. They are properly determined according to the method for detecting or quantitatively determining the peptide of the present invention. Additionally, the diagnostic reagent may contain a component in addition to the antibody of the present invention. Examples of such a component are an enzyme-labeled secondary antibody and a coloring agent.

The peptide of the present invention and Alcadein which is a precursor thereof are similar to Aβ and APP, respectively, in various respects. Therefore, it is highly suggested that a substance which suppresses the production of the peptide of the present invention also suppresses the production of Aβ. Furthermore, it is highly suggested that a substance which changes the molecular species of the peptide of the present invention from a high-molecular-weight peptide to a low-molecular-weight peptide (i.e., a peptide of the present invention other than the high-molecular-weight peptide) also changes the molecular species of Aβ from a high-molecular-weight peptide of highly toxic to other type. Therefore, it is thought that the screening for a therapeutic agent for Alzheimer's disease can be performed by contacting the cells secreting the peptide of the present invention with an agent to be screened and determining a change in the secretion of the peptide or a change in the molecular species of the secreted peptide.

The cells secreting the peptide of the present invention may be such cells that originally secrete the peptide of the present invention or may be such cells that have been transformed so as to secrete the peptide of the present invention by gene transfer. Examples of the former cells include fibroblasts (Araki, Y., et al., J. Biol. Chem. 2004, 279, 24343-24354) and HEK293 (in the Examples, an Alcadein gene is introduced into this cell, but endogenous Alcadein is expressed without the introduction). The latter cells can be prepared by introducing the full-length gene of Alcadein or a DNA encoding a first cleavage product (or a mimic construct thereof) into cells, for example. In addition, when a change in the molecular species of the peptide of the present invention is investigated, cells secreting a high-molecular-weight peptide of the present invention are preferably used. Such cells can be prepared by introducing a gene of a presenilin variant (1143F, 278T, 434C, L35F, etc.) into the cells so as to stably express the gene or inducing a mutation in the Alcadein gene, as shown in Examples 11 and 12 described below.

The method for contacting cells with an agent to be screened is not limited as long as the agent can act on the cells. Examples of the method include a method of directly inoculating an agent into cells and a method of adding an agent to a cell-culture medium.

The change in the amount of secreted peptide and the change in the molecular species of the secreted peptide can be investigated according to the method for detecting or quantitatively determining the peptide of the present invention described above. When a decrease in the secretion amount of the peptide caused by an agent to be screened is observed, the agent can be a candidate for a therapeutic agent for Alzheimer's disease When a change in the molecular species of the peptide, i.e., a change from a high-molecular-weight peptide to a low-molecular-weight peptide, caused by an agent to be screened is observed, the agent also can be a candidate for a therapeutic agent for Alzheimer's disease.

Here, the term "therapeutic agent" includes not only an agent for treating Alzheimer's disease but also an agent having a preventive effect to suppress the onset of symptoms or delay the onset of symptoms of Alzheimer's disease.

EXAMPLES

The present invention will now be described further in detail with reference to Examples.

Example 1

The brain of five 8-week-old C57BL6 mice was homogenized with 10-strokes of a loose-fit Teflon homogenizer (clearance: 0.12 μm) in 30 ml of ice-cooled buffer A (10 mM HEPES of pH 7.4, 0.32 M sucrose, 5 μg/ml chymostatin, 5 μg/ml leupeptin, and 5 μg/ml pepstatin). The homogenate was centrifuged (1000×g, 10 min) to remove unbroken cells and nuclei and to obtain a nucleus-removed cell homogenate. The nucleus-removed cell homogenate was further centrifuged (100000×g, 60 min) to obtain a pellet of a membrane fragment. The membrane fragment was resuspended in 2 ml of the buffer A and then gently overlayered on a solution (10 ml) of the buffer A with an iodixanol density-gradient of 0 to 28% in a Beckmann SW41 tube so as not to disturb the interface between the two solutions, and then centrifuged at 41000 rpm at 4° C. for 115 min. After the centrifugation, 13 fractions each of 900 ml were collected from the bottom of the tube. To 7.5 μl of each fraction, 5 μl of 5×SDS sample buffer (43% glycerol (Wako), 16% SDS (Wako), 64 ng/ml bromophenol blue (Wako), 5 mM EDTA, and 0.22 M Tris-HCl of pH 6.8) and 2.5 μl of 8 M urea solution were added. The resulting mixture was boiled for 5 min and then subjected to SDS-PAGE using an 8% gel according to the Lammli method. Proteins on the gel were transferred on a nitrocellulose membrane for performing Western blotting. The detection was performed by using an ECL kit (Pharmacia). The used antibodies were an anti-APP cytoplasmic domain antibody (reactive to both fill-length APP and a C-terminal fragment), anti-X11L antibody, anti-Alcα antibody, anti-protein disulfide-isomerase (PDI) antibody, anti-Golgi body 130 kDa matrix protein (GM-130) antibody, anti-synaptotagmin (SYT) antibody, anti-mouse kinesin heavy chain (KHC) antibody, and anti-presenilin 1 (PS1) C-terminal fragment antibody. Among them, commercially available anti-X11L antibody (mint2, BD Biosciences), anti-PDI antibody (1D3, Stressgen Biotechnologies), anti-GM130 antibody (#35, BD Biosciences), anti-SYT antibody (#41, BD Biosciences), anti-KHC antibody (H2, CHEMICON International), and anti-PS1 C-terminal fragment antibody (PS1-CTF, CHEMICON International) were used. The anti-APP cytoplasmic domain antibody was G369 and the anti-Alcα antibody was UT83. The G369 was prepared according to the method disclosed in Oishi, M., et al., Mol. Med. 1997, 3, 11-113. The UT83 was a polyclonal antibody derived from a rabbit immunized with an antigen peptide which was prepared by adding Cys to a C-terminal peptide (amino acids at positions 954 to 971) of human Alcα1 (Araki, Y., et al., J. Biol. Chem. 2003, 278, 49448-49458). FIG. 1 shows the results of the Western blotting.

Figure 2:
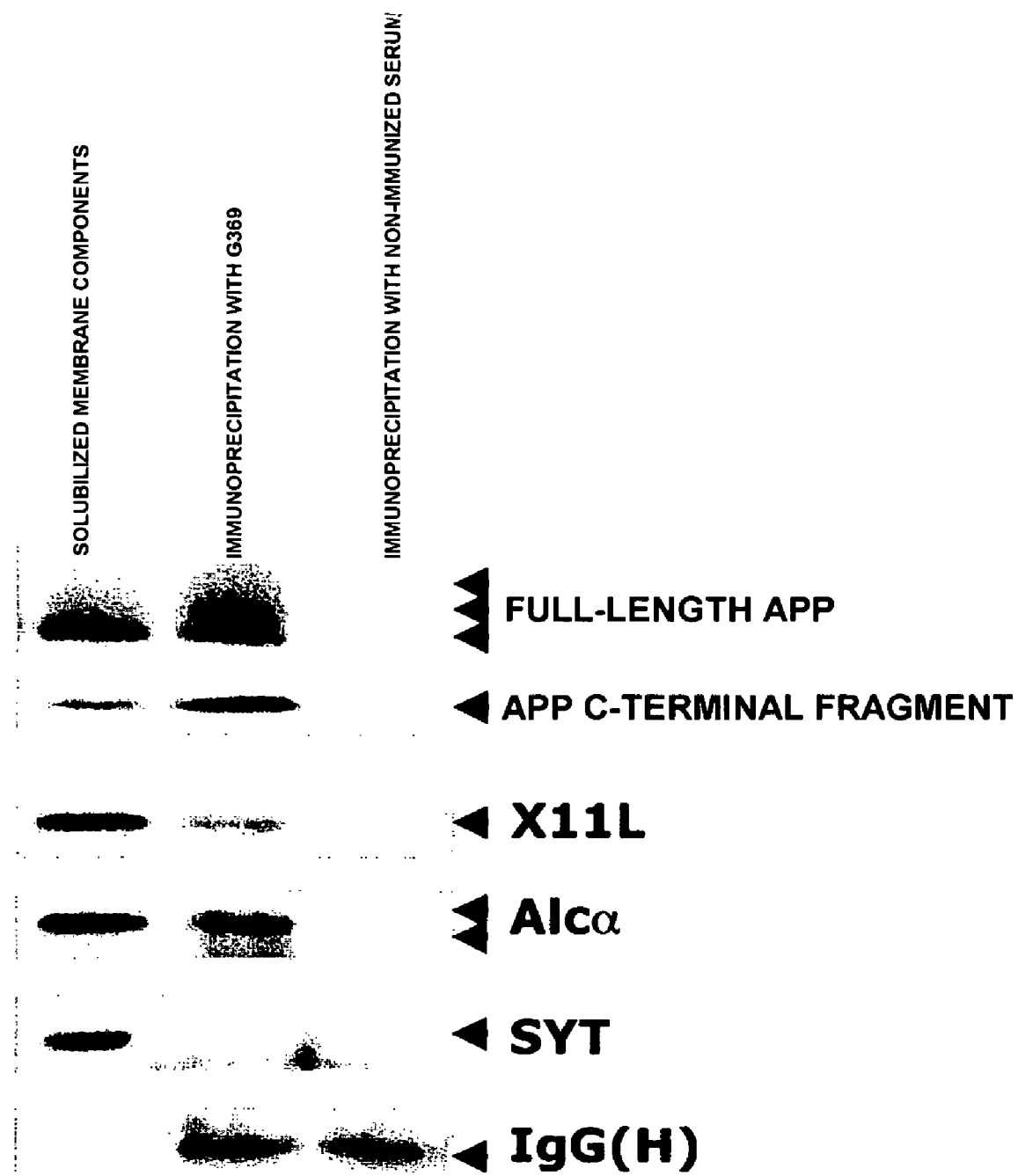
FIG. 2 is a photograph showing the results of Western blotting of proteins recovered by immunoprecipitation.

It was confirmed from the results of the Western blotting that large amounts of APP, X11L, and Alc were contained in the 8th fraction. Five hundred microliters of this fraction was added to an equal quantity of 2×CHAPS buffer (20 mM CHAPS, 20 mM sodium phosphate of pH 7.4, and 280 mM sodium chloride) to solubilize membrane components. Then, conjugate immunoprecipitation with G369 (anti-APP cytoplasmic domain antibody) was performed. Specifically, 4 μl of G369 was added to the solubilized membrane components. The resulting mixture was reacted at 4° C. for 1 hr, and then, to the mixture, 30 μl of 50% protein G-sepharose equilibrated with the 2×CHAPS buffer was further added. The resulting mixture was reacted at 4° C. for 1 hr. After the reaction, the beads were washed with 800 μl of the 2×CHAPS buffer, and then the components attached to the beads were solubilized by boiling the beads for 5 min in 45 μl of a sample-buffer mixture (a mixture of 30 μl of 5×SDS sample buffer and 15 μl of 8 M urea solution). The solubilized components were subjected to SDS-PAGE using an 8% gel, followed by Western blotting as above. An antibody against IgG heavy chain (IgG (H)), in addition to the above-used anti-APP cytoplasmic domain antibody, anti-X11L antibody, anti-Alcα antibody, and anti-SYT antibody, was also used. In addition, as a control, components obtained by conjugate immunoprecipitation using an equal quantity of non-immunized rabbit serum instead of G369 were also subjected to Western blotting. Furthermore, similarly, the solubilized membrane components before the conjugate immunoprecipitation were also subjected to Western blotting. FIG. 2 shows the results.

As shown in FIG. 2, the components obtained by the conjugate immunoprecipitation with G369 contain not only APP but also X11L and Alcα. Therefore, it is thought that APP binds to X11L and Alcα to form a complex composed of the three.

Example 2

Frontal lobe tissues derived from 5 Alzheimer's disease patients were fixed in Kryofix (a mixture of ethanol, polyethylene glycol, and water: Merck) for 1 to 7 days and embedded in paraffin. The embedded tissues were cut into serial sections with a thickness of 4 μm. The sections were de-paraffined and then immunostained using ABC elite kit (Vector Laboratory).

The immunostain was performed by incubating the sections in a 0.8 μg/ml anti-Alcα antibody (UT83) solution or a 0.5 μg/ml anti-APP extracellular domain antibody (22C11: Roche Diagnostics) solution, reacting a secondary antibody with them, and visualizing the peroxidase activity by using a diaminobenzidine-hydrogen peroxide solution. As a control, the sections were incubated in a 0.8 μg/ml non-immunized rabbit IgG solution and similarly immunostained. Additionally, the sections were incubated in a solution containing both the anti-Alcα antibody and its antigen peptide (40 nM) and similarly immunostained.

Figure 3:
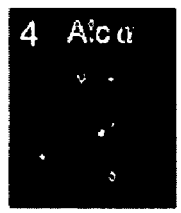
FIG. 3 is photographs of immunostained brain sections from an Alzheimer's disease patient (Alcα and APP were detected).
Figure 3:
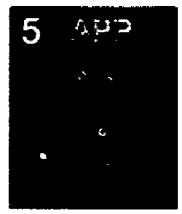
Figure 3:
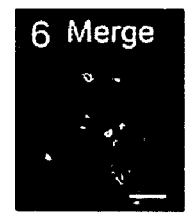

FIGS. 3-1, 3-2, and 3-3 show the results of the immunostain performed using the anti-Alcα antibody, anti-APP extracellular domain antibody, and non-immunized rabbit IgG, respectively.

As shown in these Figures, Alcα and APP are detected at similar brain regions of Alzheimer's disease patients. When the antigen peptide of the anti-Alcα antibody was presented in the solution (the results are not shown), nothing was detected as in the results shown in FIG. 3-3.

Example 3

The sections prepared in Example 2 were de-paraffined and incubated in a solution containing an anti-Alcα antibody (0.8 μg/ml) and an anti-APP extracellular domain antibody (0.5 μg/ml) or a solution containing an anti-Alcα antibody (0.8 μg/ml) and an anti-Aβ antibody (1/1000 dilution). As the anti-Aβ antibody, 4G8 (Sigma Lab) was used.

Then, the sections were incubated in solutions which each contain antibodies at the respective combinations, and then further incubated in a solution containing an FITC-labeled anti-rabbit IgG goat antibody (Jacson immunoresearch lab., 1/30 dilution) and a Cy3-labeled anti-mouse IgG goat antibody (Jacson immunoresearch lab., 1/50 dilution). The autofluorescence of lipofuscin granules was quenched by Sudan Black B staining before the immunoreaction.

Figure 4:
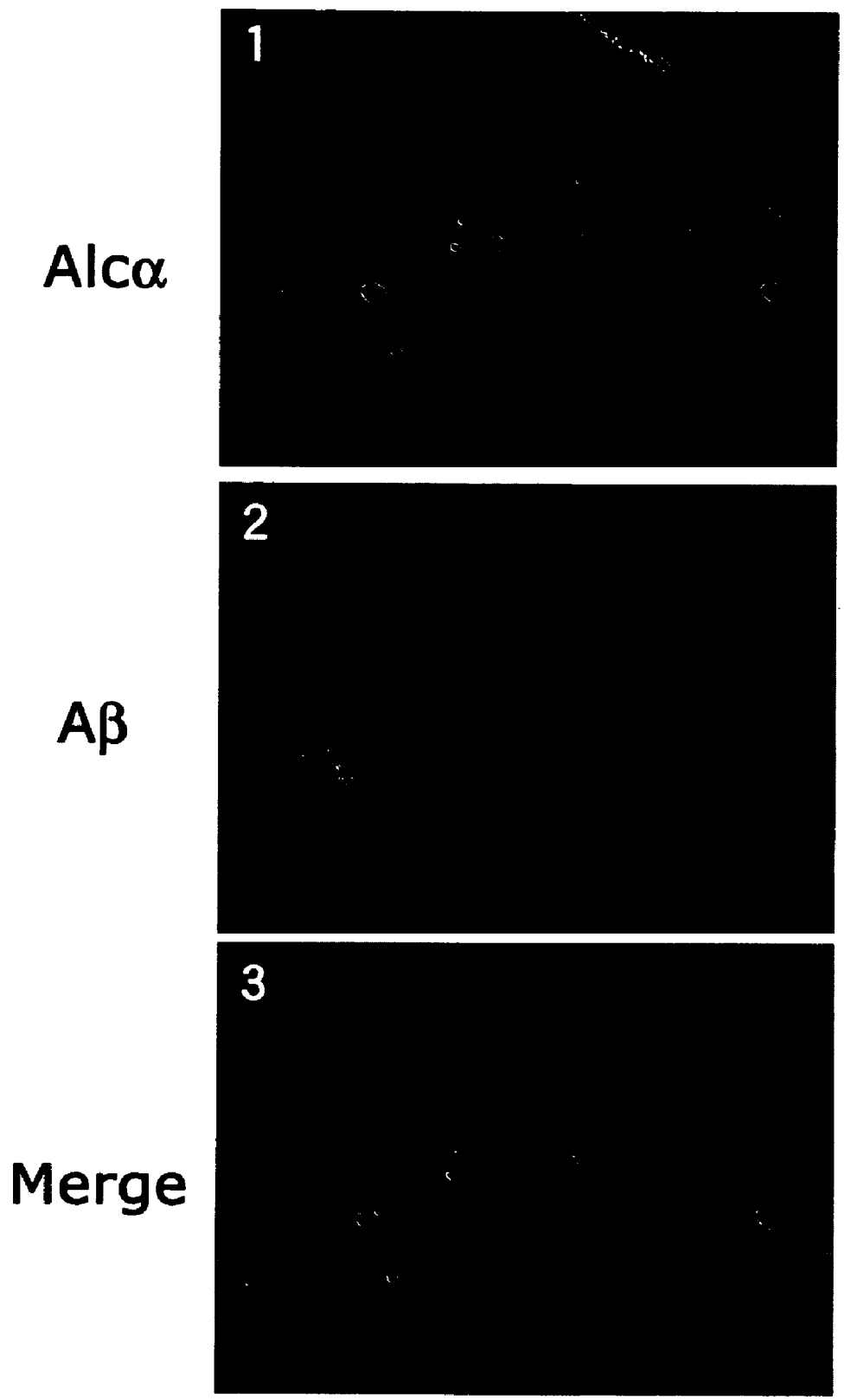
FIG. 4 is photographs of immunostained brain sections from an Alzheimer's disease patient (Alcα and Aβ were detected).
Figure 5:
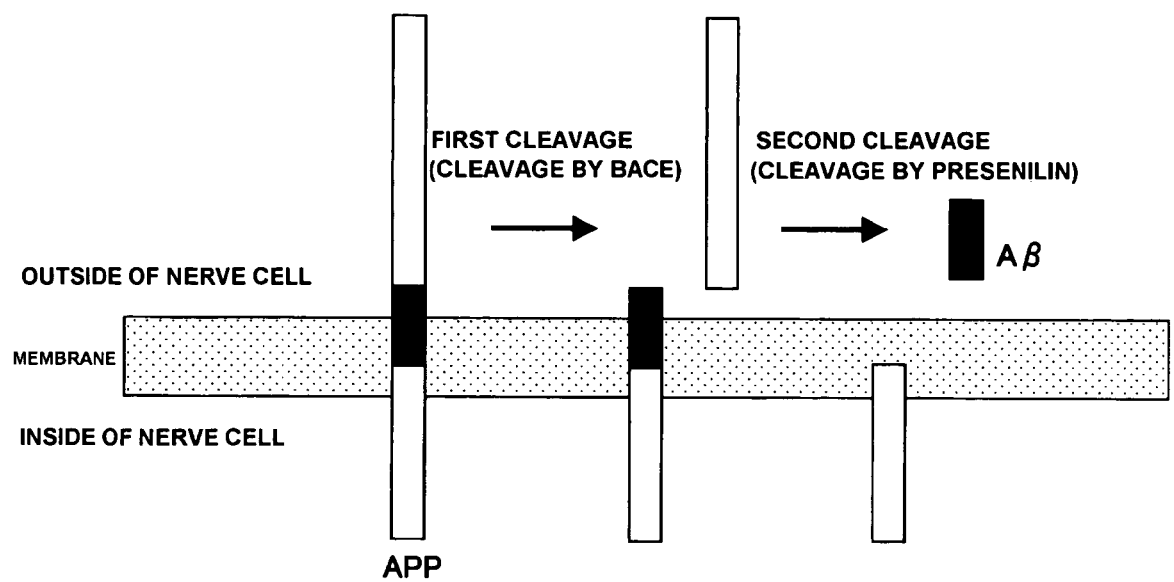
FIG. 5 is a diagram schematically illustrating a process of obtaining Aβ from APP.

The results when the anti-Alcα antibody and the anti-APP extracellular domain antibody were used as the primary antibodies are shown in FIG. 3-4 (only FITC was detected), FIG. 3-5 (only Cy3 was detected), and FIG. 3-6 (both FITC and Cy3 were detected). The results when the anti-Alcα antibody and the anti-Aβ antibody were used as the primary antibodies are shown in FIG. 4-1 (only FITC was detected), FIG. 4-2 (only Cy3 was detected), and FIG. 4-3 (both FITC and Cy3 were detected).

As shown in FIGS. 3-4, 3-5, and 3-6, Alcα and APP were detected at similar brain regions of Alzheimer's disease patients. This result agrees with that in Example 2. Additionally, as shown in FIGS. 4-1, 4-2, and 4-3, APP was detected in the vicinity of regions where senile plaques were formed by the accumulation of Aβ.

From the above-mentioned results, it is suggested that APP and Alcα similarly act in the pathogenesis process of Alzheimer's disease.

Example 4

A DNA encoding Alcα, Alcβ, Alcγ, or APP695 (an isoform of human APP consisting of 695 amino acids) was inserted into a mammalian expression vector pcDNA3.1 (Invitrogen).

HEK293 cells were seeded in DMEM (D5796: Sigma) containing 10% fetal bovine serum in a 6-well culture plate (area of base: 10 cm$^2$) and transfected with the expression vector prepared above by using a transfection reagent (LipofectAMINE 2000: Invitrogen). As a control, HEK293 cells were similarly transfected with an empty pcDNA3.1 vector.

One microliter of a DMSO solution containing 1 mM of a presenilin inhibitor L-685,458 (Calbiochem) was added to 1 ml of the culture medium. After the incubation for 24 hrs, a sample of the culture medium was taken. As a control, an equal quantity of DMSO instead of the L-685,458 solution was added to the culture medium and similarly incubated. Then, a sample of the culture medium was taken. The sample of the culture medium was added to 1 ml of HBST buffer (10 mM HEPES of pH 7.4, 150 mM sodium chloride, 0.5% Triton X-100, 5 μg/ml chymostatin, 5 μg/ml leupeptin, and μg/ml pepstatin) for extracting proteins of the cells. The solubilized cells were centrifuged (12000×g, 10 min) and supernatant was collected to recover the solubilized components. The solubilized components (7.5 μl) were added to 7.5 μl of a sample-buffer mixture (a mixture of 5 μl of 5×SDS sample buffer and 2.5 µl of 8 M urea solution) and boiled for 5 min. This sample was subjected to SDS-PAGE of 8/15% 2-stage gel and then the proteins were transferred on a nitrocellulose membrane for conducting Western blotting. The SDS-PAGE was performed according to the general method of Laemmli. As the primary antibody, an anti-APP cytoplasmic domain antibody (G369, 1/2000 dilution), anti-Alcα antibody (UT83, 0.3 µg/ml), anti-Alcβ antibody (UT99, 0.5 µg/ml), and anti-Alcγ antibody (UT105, 1/500 dilution) were used. The detection was performed by using an ECL kit (Pharmacia). The UT99 and UT105 are antibodies recognizing the C-terminals of Alcβ and Alcγ, respectively. FIG. 6 and FIG. 7A to C show the results.

Figure 6:
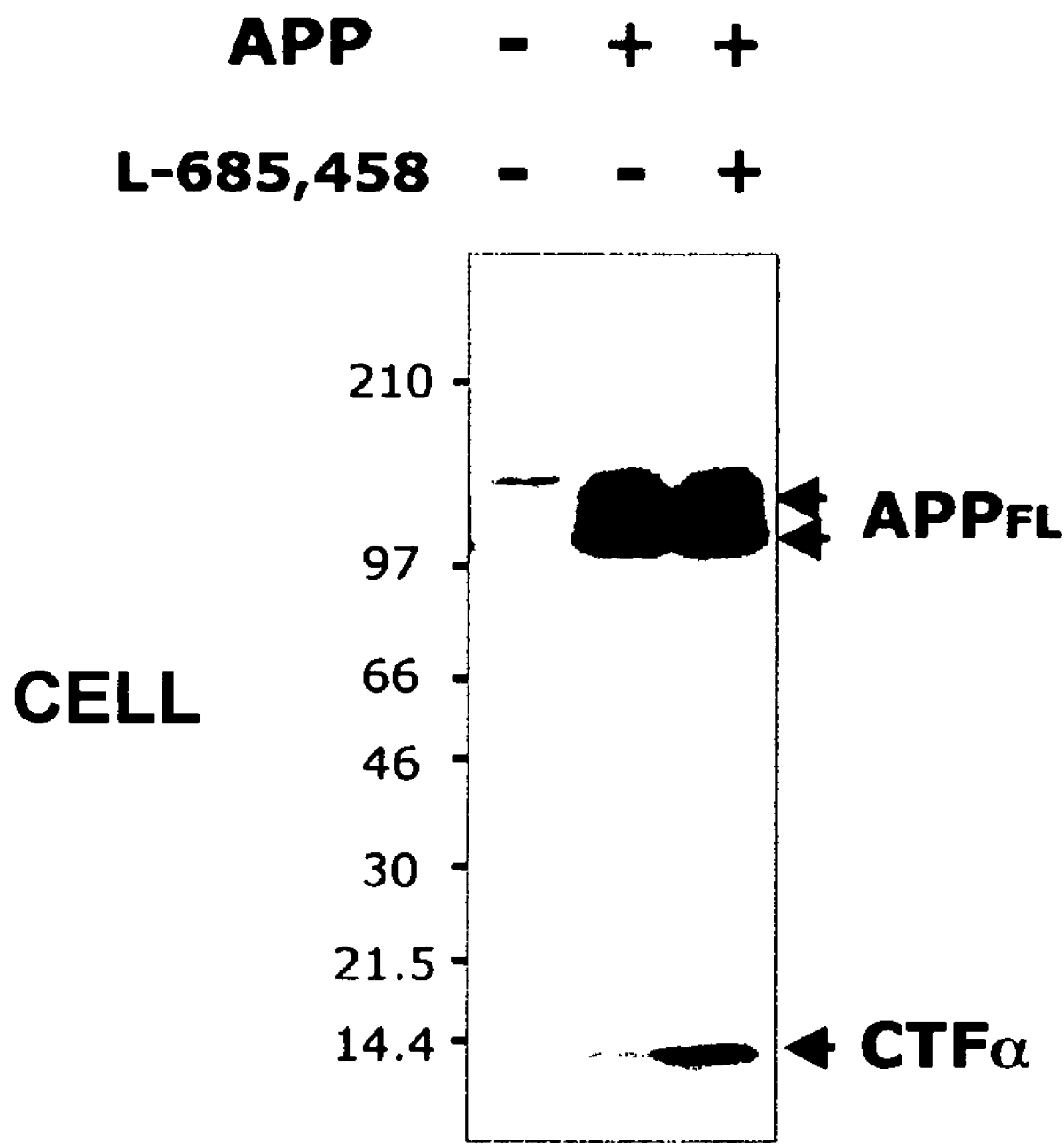
FIG. 6 is a diagram showing the results of Western blotting of cell lysates using an anti-APP antibody.

The C-terminal fragment obtained by a primary cleavage of APP is secondarily cleaved by presenilin, and the resulting cleavage fragment is extracellularly secreted (FIG. 5). At this point, the secondary cleavage is inhibited by adding a presenilin inhibitor and the C-terminal fragment of APP is accumulated inside cells. As shown in FIG. 6, this fact is reflected to the result that a large amount of the C-terminal fragment (CTFα) was detected in the cell lysate only when the presenilin inhibitor (L-685,458) was added.

Figure 7:
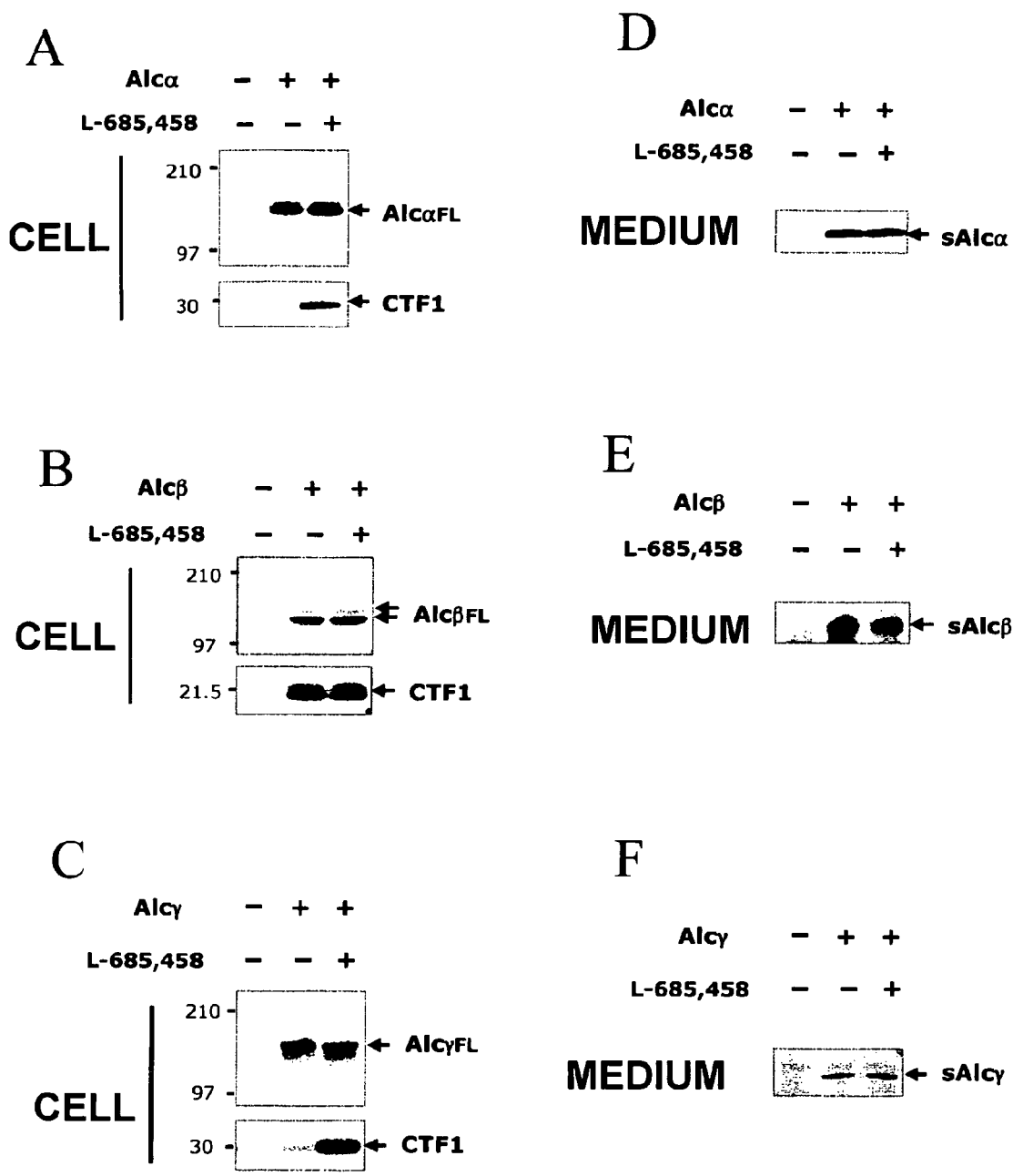
FIG. 7 is diagrams showing the results of Western blotting of cell lysates using an anti-Alc antibody and media using an anti-FLAG antibody.

In the cases of Alcα and Alcγ, similarly to the case of APP, C-terminal fragments (CTF1) were detected only when the presenilin inhibitor was added (FIGS. 7A and C). From these results, it is thought that the C-terminal fragments of Alcα and Alcγ are cleaved by presenilin as in APP. However, the C-terminal fragment of Alcβ was detected even when the presenilin inhibitor was not added (FIG. 7B). Therefore, it is not confirmed whether the C-terminal fragment of Alcβ is cleaved by presenilin from this experiment only.

Example 5

DNAs encoding proteins (FLAG-Alcα, FLAG-Alcβ, and FLAG-Alcγ), Alcα, Alcβ, or Alcγ including a FLAG-tag sequence downstream of the N-terminal signal sequence thereof, were prepared. Each of the proteins was inserted into a mammalian expression vector pcDNA3.1 (Invitrogen).

HEK293 cells were seeded in DMEM (D5796: Sigma) containing 10% fetal bovine serum in a 6-well culture plate (area of base: 10 cm$^2$) and the cells were transfected with the expression vector prepared above by using a transfection reagent (LipofectAMINE 2000: Invitrogen). As a control, HEK293 cells were transfected with an empty pcDNA3.1 vector.

One microliter of a DMSO solution containing 1 mM presenilin inhibitor L-685,458 (Calbiochem) was added to 1 ml of the culture medium. After the incubation for 24 hrs, a sample of the culture medium was taken. As a control, an equal quantity of DMSO instead of the L-685,458 solution was added to the culture medium and similarly incubated. Then, a sample of the culture medium was taken.

One hundred and fifty microliters of buffer B (7.7% SDS, 16.7 mM Tris-HCl of pH7.4, 0.3 mg/ml chymostatin, 0.3 mg/ml leupeptin, and 0.3 mg/ml pepstatin) was added to 1 ml of the culture medium and boiled for 5 min to denature the protein components. Then, 3.75 ml of buffer C (6.7% NP-40, 0.4 M NaCl, 26 mM EDTA, and 200 mM Tris-HCl of pH 7.4) and 1.75 ml of an enzyme inhibition solution (distilled water containing 10 ng/ml leupeptin, 10 ng/ml pepstatin A, and 10 ng/ml chymostatin) were sequentially added. After the addition of 2 µl of anti-FLAG antibody (Sigma), the resulting mixture was mixed by inverting the tube in a low-temperature chamber (4° C.) for 8 hrs for an antigen-antibody reaction. Then, 50 µl of rinse buffer (0.1% Triton X-100, 1 mM EDTA, 150 mM NaCl, and 10 mM Tris-HCl of pH 7.4) containing 25% protein G-sepharose/25% sepharose 4B (Pharmacia Biotech) was added, and the tube was rotated at 4° C. for 3 hrs. The resin components were precipitated by centrifugation (3000 rpm, 5 min, 4° C.) and recovered. The recovered resins were washed, in order to eliminate non-specific binding, with washing buffer I (0.1% Triton X-100, 1 M NaCl, and 20 mM Tris-HCl of pH 7.4), washing buffer II (0.05% SDS, 1% Triton X-100, 5 mM EDTA, 150 mM NaCl, and 50 mM Tris-HCl of pH 7.4), and the rinse buffer, sequentially. Then, 30 µl of a sample-buffer mixture (a mixture of 20 µl of 5×SDS sample buffer and 10 µl of 8 M urea solution) was added to the resins and mixed. The mixture was boiled for 5 min for solubilizing components which were attached to the resins. After the centrifugation, the supernatant components were subjected to SDS-PAGE using a 6% gel and then the proteins were transferred on a nitrocellulose membrane for conducting Western blotting. The SDS-PAGE was performed according to the general method of Lammli. As the primary antibody, an anti-FLAG antibody (M2, Sigma) was used. The detection was performed by using an ECL kit. FIG. 7D to F show the results.

As shown in these Figures, fragments which can be recognized by the anti-FLAG antibody were detected in all culture media of Alcα, Alcβ, and Alcγ. Since the FLAG tag sequence was bound to the N-terminal of mature Alcα, Alcβ, and Alcγ, it is thought that the N-terminal fragments obtained by the primary cleavage of Alcα, Alcβ, and Alcγ are secreted extracellularly.

Example 6

DNAs encoding Alcα, Alcβ, or Alcγ were each inserted into a mammalian expression vector pcDNA3.1 (Invitrogen).

HEK293 cells were seeded in DMEM containing 10% fetal bovine serum in a 10-cm culture plate (area of base: 60 cm$^2$) and transfected with the expression vector prepared above by using a transfection reagent (LipofectAMINE 2000: Invitrogen). As a control, HEK293 cells were transfected with an empty pcDNA3.1 vector.

After the incubation for 24 hrs, the culture medium was removed and the cells were washed with ice-cooled PBS. Then, 10 ml of PBS was added again. The cells were detached from the plate by pipetting and transferred into a 15 ml Falcon tube. The cells were collected by centrifugation (1500 rpm, 10 min, low-speed refrigerated centrifuge: Beckmann) as a pellet of the cells. One milliliter of buffer D (0.25 M sucrose, 10 mM triethanolamine-acetate of pH 7.8, 5 µg/ml chymostatin, 5 µg/ml leupeptin, and 5 µg/ml pepstatin) was added to the pellet of the cells, and the cells were broken by 12 passages through a 27 G needle. Then, the broken cells were centrifuged with a TOMY TMA-6 rotor at 3000 rpm (1000× g) for 10 min at 4° C. to remove unbroken cells and nuclei and to obtain a nucleus-removed cell homogenate. The nucleus-removed cell homogenate was further centrifuged with a Beckmann TLA-45 rotor at 45000 rpm (100000×g) for 60 min at 4° C. to obtain a supernatant (cytoplasm fragment) and a precipitate (membrane fragment). The membrane fragment was resuspended in 100 µl of the buffer D.

Figure 8:
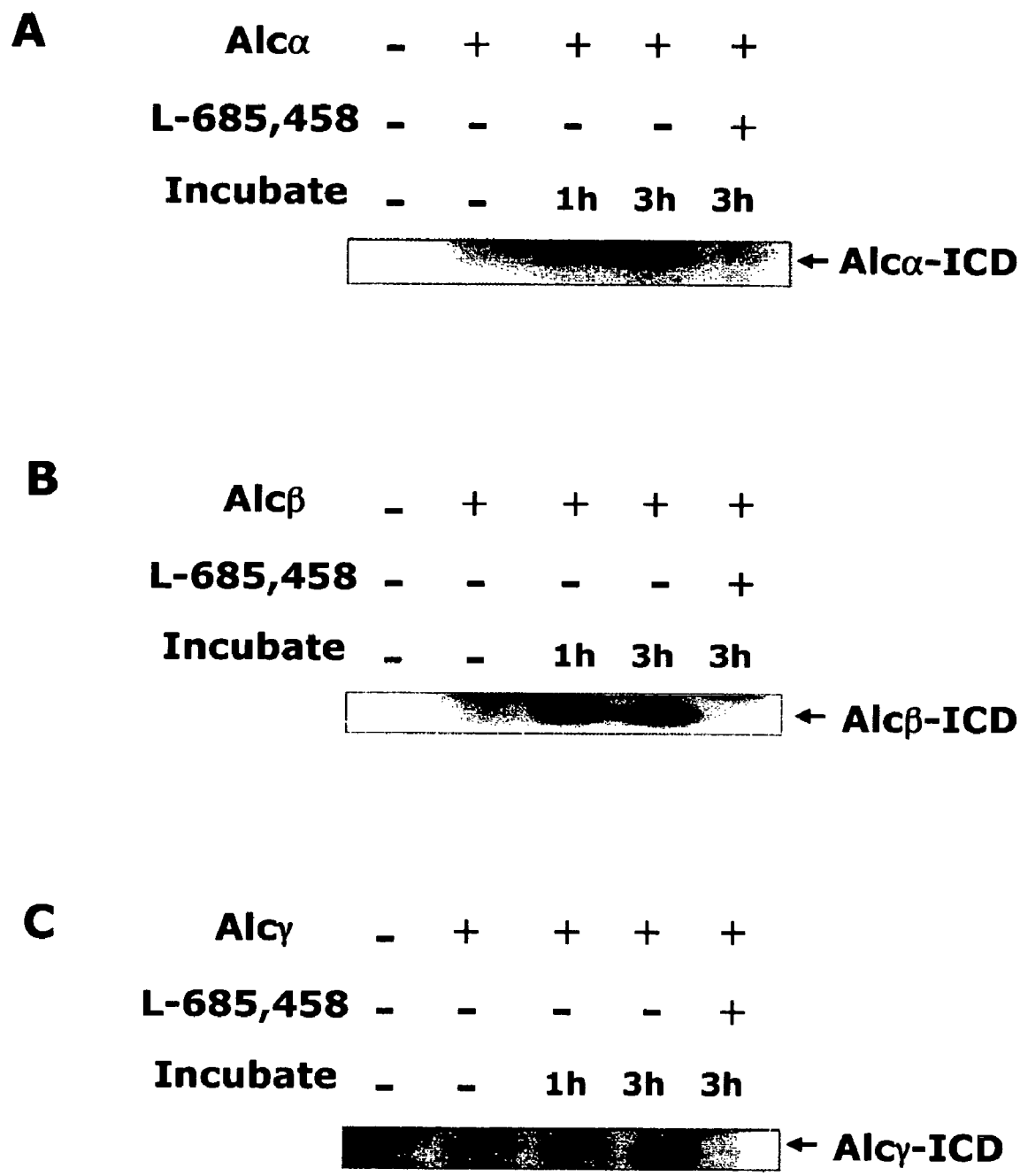
FIG. 8 is diagrams showing the results of Western blotting of membrane fractions using an anti-Alc antibody.

A sample of 20 µl of the resuspended membrane-fragment was incubated at 37° C. for 1 or 3 hrs. Separately, a sample of the resuspended membrane-fragment to which a presenilin inhibitor (L-685,458) was added at a final concentration of 1 µM was also prepared. Twenty microliters of a sample-buffer mixture (a mixture of 13.4 µl of 5×SDS sample buffer and 6.6 µl of 8 M urea solution) was added to each sample for terminating the reaction. The sample was boiled for 5 min and was subjected to SDS-PAGE using 8/15% 2-stage gel. Then, the proteins were transferred on a nitrocellulose membrane for conducting Western blotting. The SDS-PAGE was performed according to the general method of Lammli. As the primary antibody, an anti-Alcα antibody (UT83), anti-Alcβ antibody (UT99), and anti-Alcγ antibody (UT105) were used. The detection was performed by using an ECL kit (Pharmacia) FIG. 8A to C shows the results.

As shown in these Figures, fragments (such as Alcα-ICD) containing the C-terminal of each Alc were detected by incubating the membrane fragments of Alcα, Alcβ, and Alcγ. However, such fragments were not detected in the samples to which the presenilin inhibitor was added. On the basis of the results above, it is thought that a fragment containing the C-terminal of Alcα and so on was cleaved by presenilin.

Example 7

Figure 9:
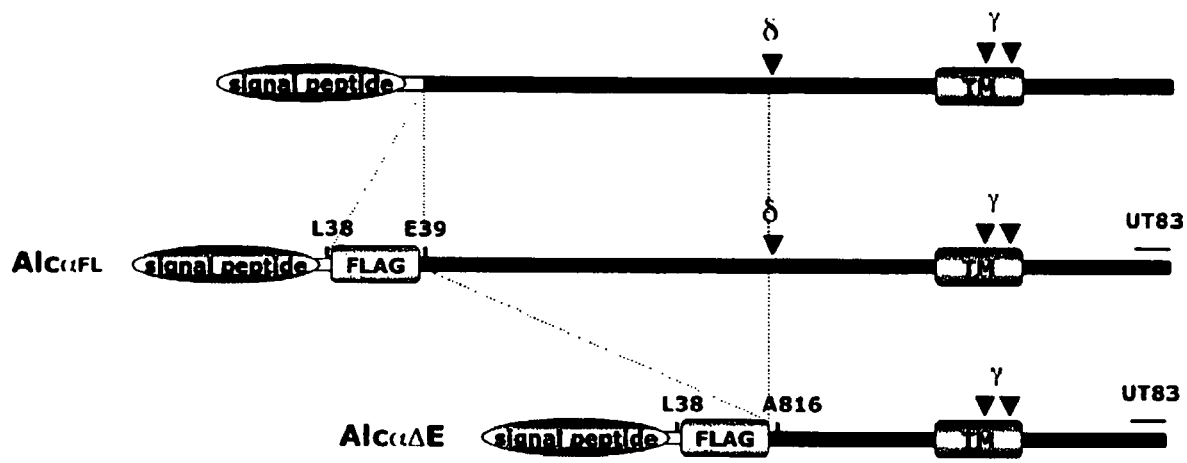
FIG. 9 is a diagram illustrating a structure of AlcαΔE.

A DNA encoding AlcαΔE was prepared for efficiently detecting a cleavage product (Aβ-like fragment) obtained by a secondary cleavage of Alcα. As shown in FIG. 9, in AlcαΔE, a fragment between the signal peptide and the primary cleavage site (indicated by δ in the Figure) was removed and the FLAG-tag sequence was introduced into the C-terminal end of the signal peptide.

A DNA encoding AlcαΔE was inserted into a mammalian expression vector pcDNA3.1 (Invitrogen). HEK293 cells were seeded in DMEM containing 10% fetal bovine serum in a 10-cm culture plate (area of base: 60 cm$^2$) and transfected with the expression vector prepared above by using a transfection reagent (LipofectAMINE 2000: Invitrogen). As a control, HEK293 cells were similarly transfected with an empty pcDNA3.1 vector. A DMSO solution containing 10 μM LLnL (Calbiochem), 1 μM DAPT (Calbiochem), or 1 μM L-685,458 (Calbiochem), which are presenilin inhibitors, was added to 1 ml of the culture medium at a final concentration of 1 μM. After the incubation for 24 hrs, a sample of the culture medium was taken. As a control, an equal quantity of DMSO instead of the solution of the presenilin inhibitors such as L-685,458 was added to the culture medium and similarly incubated. Then, a sample of the culture medium was taken.

The recovered media were each subjected to immunoprecipitation using an anti-FLAG antibody (M2: Sigma) and Western blotting to detect a presenilin-induced N-terminal cleavage product. Specifically, 4 μl of the anti-FLAG antibody was added to each recovered culture medium and reacted at 4° C. for 1 hr. Then, 30 μl of rinse buffer (0.1% Triton X-100, 1 mM EDTA, 150 mM NaCl, and 10 mM Tris-HCl of pH 7.4) containing 50% protein G-sepharose was added and further reacted at 4° C. for 1 hr. Then, the beads were recovered and washed with 800 μl of each of the washing buffer I (the composition is the same as in Example 5), the washing buffer II (the composition is the same as in Example 5), and the rinse buffer (the composition is the same as in above) sequentially. Then, the beads were boiled in 30 μl of 2×tricine-sample buffer (900 mM Tris-HCl of pH 8.45, 24% glycerol, 8% SDS, and 0.005% Coomassie brilliant blue) for 5 min to solubilize components which were attached on the beads. The solubilized components were separated by using a 15% Tris-Tricine gel (as per Schagger & von Jagow method) and subjected to Western blotting using an anti-FLAG antibody (1/2000 dilution) and an anti-Alcα antibody (UT83). The presenilin-induced cleavage product (Aβ-like fragment) and AlcαΔE were detected by an ECL kit (Pharmacia).

Figure 10:
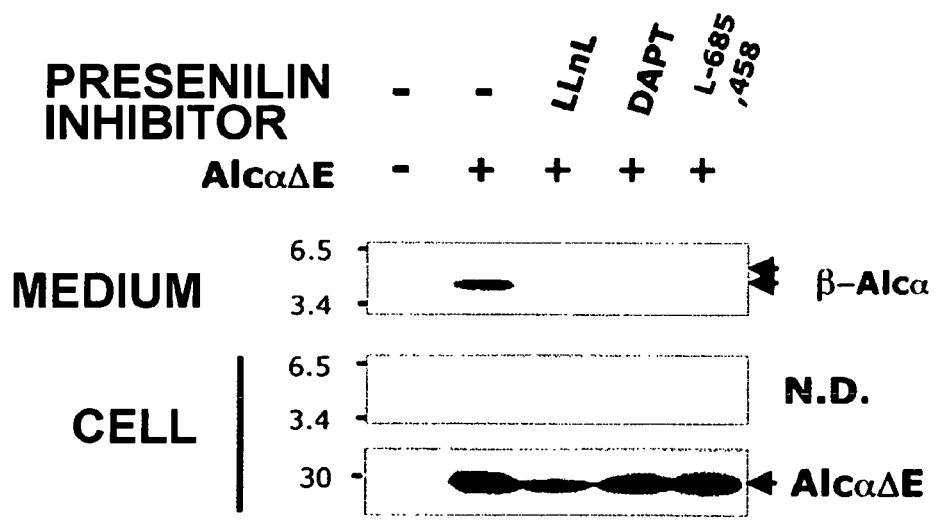
FIG. 10 is a diagram showing the results of Western blotting of cell lysates and an medium using an anti-FLAG antibody.

At the same time, cells were subjected to immunoprecipitation and Western blotting. Specifically, proteins were extracted from the cells in 4 ml of HBST buffer (the composition is the same as in Example 4). The solubilized cells were centrifuged (12000×g, 10 min) and the supernatant was collected to recover the solubilized components. Two microliters of the anti-FLAG antibody was added to 1 ml of the solubilized components and the mixture was reacted for 1 hr. Then, 30 μl of HBST buffer containing 50% protein G-sepharose was added and further reacted at 4° C. for 1 hr. Then, the beads were recovered and washed with 800 μl of the HBST buffer 3 times. Then, the beads were boiled in 45 μl of a sample-buffer mixture (a mixture of 30 μl of a 5×SDS sample buffer and 15 μl of 8 M urea solution) for 5 min to solubilize components which were attached on the beads. The solubilized components were separated by using a 15% Tris-Tricine gel (as per Lamili method) and subjected to Western blotting using an anti-FLAG antibody (1/2000 dilution) and an anti-Alcα antibody (UT83). FIG. 10 shows the results mentioned above.

As shown in FIG. 10, AlcαΔE which was transfected into the cells were detected in the cell lysates, but the presenilin-induced cleavage product (β-Alcα) was detected only in the culture media and was not detected in the cell lysates. From these results, it is thought that the presenilin-induced cleavage fragment has a property that the majority is secreted into the culture medium, as in Aβ.

Example 8

DNAs encoding Alcα or APP695 were each inserted into a mammalian expression vector pcDNA3.1 (Invitrogen), and a DNA (provided from Dr. Doms) encoding human BACE 1 was inserted into a mammalian expression vector pcDNA3.1Zeo(+) (Invitrogen).

HEK293 cells were seeded in DMEM (D5796: Sigma) containing 10% fetal bovine serum in a 6-well culture plate (area of base: 10 cm$^2$) and transfected with the expression vector prepared above by using a transfection reagent (LipofectAMINE 2000: Invitrogen). Combinations of the introduced DNAs are shown in FIG. 11.

Each of the cells was incubated for 24 hrs. Proteins of the cells were solubilized in HBST buffer (the composition is the same as in Example 4) and subjected to SDS-PAGE using 8/15% gel. The proteins on the gel were transferred on a nitrocellulose membrane for conducting Western blotting using an anti-APP antibody (APP/c, Sigma) and an anti-Alcα antibody (UT83 antibody) FIGS. 11A and B show the results of Western blotting using the anti-APP antibody and ant-Alcα antibody, respectively.

As shown in FIG. 11A, in the cells not expressing BACE1 (3rd lane from the left), CTFα, which is a cleavage product at the α-site, was mainly detected, but in the cells expressing BACE1 (4th lane from the left), CTFβ, which is a cleavage product at the β-site, was also detected. Additionally, only two bands indicated by arrows correspond to APP695 are and another two bands detected in the vicinity thereof correspond to endogenous APPs (APP770 and APP751).

Figure 11:
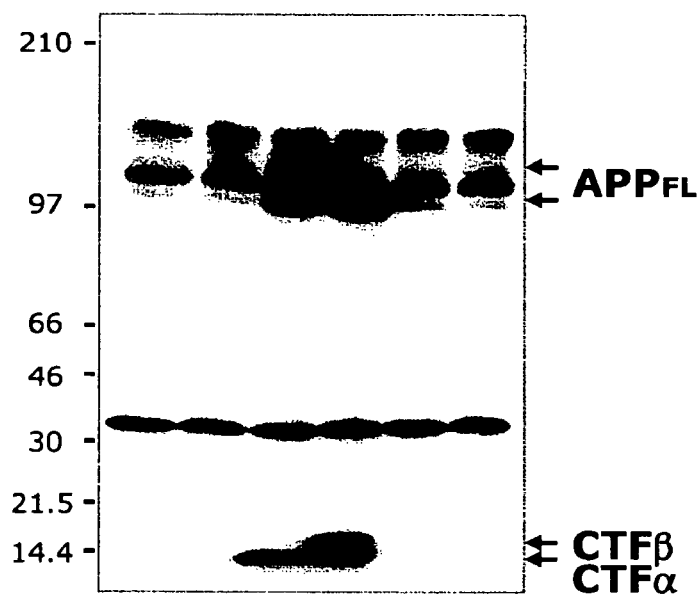
FIG. 11 is diagrams showing the results of Western blotting of cell lysates expressing APP or Alcα and BACE1.
Figure 11:
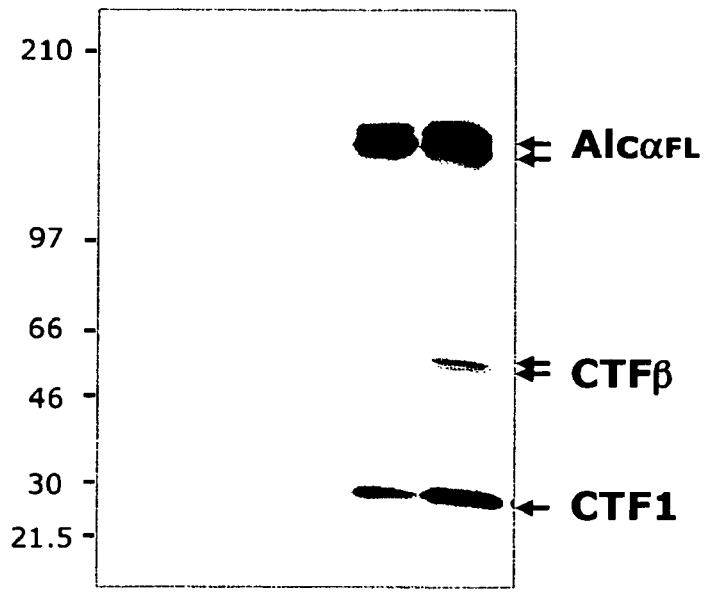

As shown in FIG. 11B, in the cells expressing Alcα but not expressing BACE1 (5th lane from the left), a fragment (CTF1) was mainly detected at a position of 30 kDa. Since the molecular weight of this fragment was approximately equal to that of AlcαΔE expressed in Example 7, it is predicted that the cleavage site is between Met-815 and Ala-816 or in the vicinity thereof and that the number of amino acids is about 156. In the cells expressing both Alcα and BACE1 (6th lane from the left), CTF1 and a fragment (CTFβ, the number of amino acid residues calculated from the molecular weight is about 280) with a molecular weight larger than that of CTF1 were detected. It is thought that this fragment is generated when Alcα is cleaved by BACE1. Namely, it is thought that Alcα is cleaved by BACE1 as in APP. Additionally, with reference to FIG. 11, Alcα is detected as two bands. This is due to sugar chain modification.

Example 9

Figure 12:
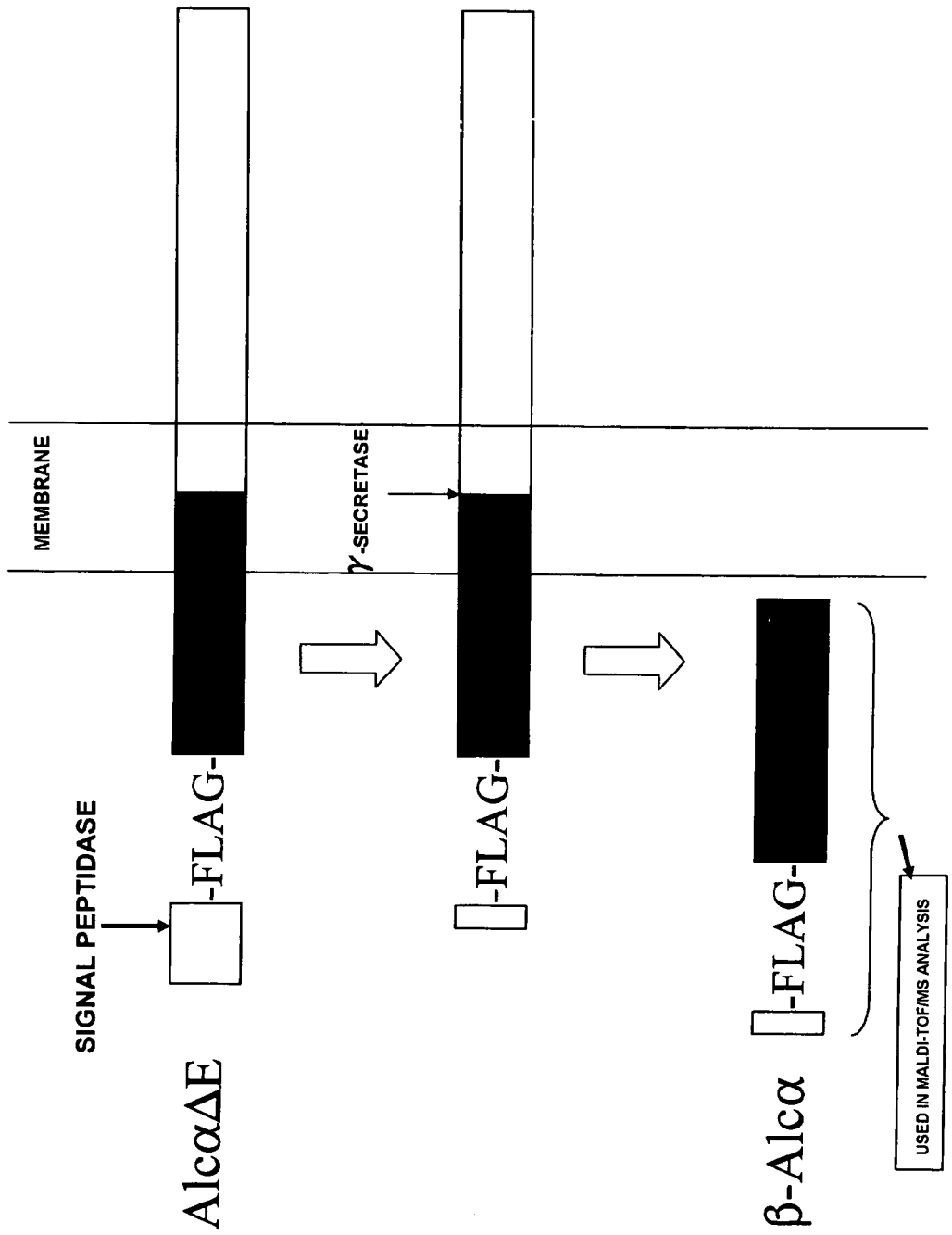
FIG. 12 is a diagram schematically illustrating a process of preparing β-Alcα (a peptide obtained by cleaving an N-terminal region and a C-terminal region of Alcα) including a FLAG sequence.

The cleavage site of γ-secretase in Alcα was identified as follows: A cDNA construct (FIG. 9) expressing AlcαΔE protein was prepared. As shown in FIG. 12, cells transfected with this cDNA construct produce and secrete β-Alcα having a FLAG-tag sequence. The β-Alcα secreted by the cells was recovered by immunoprecipitation using an anti-FLAG antibody, and the molecular weight of the immunoprecipitate was analyzed by using a MALDI-TOF/MS. On the basis of this molecular weight, the cleavage site of γ-secretase was identified. The details will now be described.

(1) Analysis of β-Alcα having a FLAG Sequence by Western Blotting

HEK293 cells were seeded in a 10-cm dish (Corning). When the cells became confluent, the cells were transfected with an expression vector of AlcαΔE (pcDNA3-FLAG-hAlcαΔE) by using a transfection reagent (LipofectAMINE 2000: Invitrogen). The cells were incubated in a $CO_2$ incubator for 24 hrs. Hereat, 2 μl of a DMSO solution containing 1 mM γ-secretase inhibitor L-685,458 (Calbiochem) was added to 1 ml of the culture medium. As a control, cells to which added only the DMSO solution were also prepared. Six milliliters of each culture medium was recovered and centrifuged (15000 rpm, 5 min, high-speed refrigerated microcentrifuge: TOMY). To the resulting supernatant, 1/1000 volume of an enzyme inhibition solution (a DMSO solution containing 5 mg/ml leupeptin, 5 mg/ml pepstatin A, and 5 mg/ml chymostatin) was added to prepare a sample for immunoprecipitation. This sample was mixed with 6 μl of an anti-FLAG antibody solution (M2: Sigma) by inverting at 4° C. for 1 hr. Then, to the mixture, 50 μl of rinse buffer (10 mM Tris-HCl of pH 7.4, 1 mM EDTA, 0.1% Triton X-100, and 150 mM NaCl) containing 25% protein G-sepharose was added, and an antigen-antibody reaction was conducted by mixing by inverting the mixture at 4° C. for 1 hr. After the reaction, the beads were precipitated and recovered by centrifugation (3000 rpm, 5 min, 4° C., high-speed refrigerated microcentrifuge: TOMY SEIKO CO., LTD.), and washed with washing buffer 1 (1 M NaCl, 20 mM Tris-HCl of pH 7.4, and 0.1% Triton X-100), washing buffer 2 (150 mM NaCl, 5 mM EDTA, 50 mM Tris-HCl of pH 7.4, 1% Triton X-100, and 0.05% SDS), and rinse buffer, sequentially. Then, the beads were stirred in 20 μl of a sample-buffer mixture (a mixture of 10 μl of 2×SDS sample buffer and 10 μl of 8 M urea solution) and then boiled for 5 min to elute components which were adsorbed on the beads. After the centrifugation, the supernatant components were separated by 20% acrylamide Tris-Tricine gel electrophoresis and then subjected to Western blotting using an anti-FLAG antibody (M2: Sigma). The reacting β-Alc having the FLAG-tag was detected by an ECL kit (Pharmacia).

Ice-cooled PBS (1.5 ml) was added to the cells isolated from the culture medium. Then, the cells were detached from the plate by pipetting and transferred into an eppendorf tube. The cells were collected by centrifugation (6000 rpm, 5 min, high-speed refrigerated microcentrifuge: TOMY SEIKO CO., LTD.). The resulting cell pellet was mixed with 0.9 ml of HBST buffer (the composition is the same as in Example 4) by inverting at 4° C. for 1 hr to extract proteins of the cells. The solubilized cells were centrifuged (15000 rpm, 15 min, 4° C., high-speed refrigerated microcentrifuge: TOMY SEIKO CO., LTD.) to recover the solubilized components as the supernatant. To 5 μl of the solubilized components, 10 μl of 2×SDS sample buffer and 5 μl of 1% SDS were added. The resulting mixture was boiled for 5 min. The solubilized components were separated by 20% acrylamide Tris-Tricine gel electrophoresis and then transferred to a nitrocellulose membrane (S&S). After the reaction with an anti-FLAG antibody (M2: Sigma), the reaction product was detected by an ECL kit (Pharmacia) on the membrane.

Figure 13:
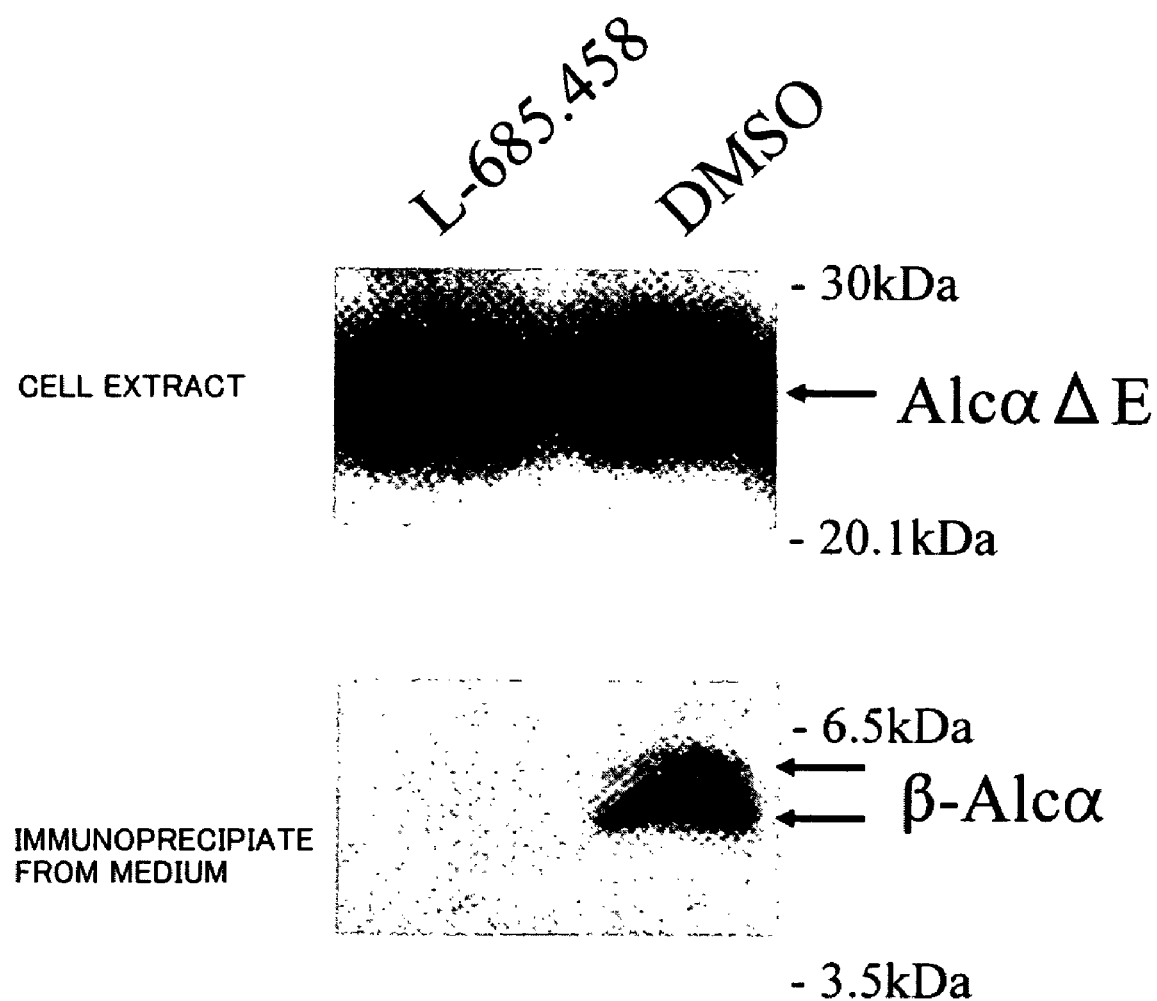
FIG. 13 is diagrams showing the results of Western blotting of an extract solution of cells expressing AlcαΔ and immunoprecipitate of a medium when an anti-FLAG antibody is used.

FIG. 13 shows the results of the Western blotting mentioned above. In the immunoprecipitate sample of the culture medium, β-Alcα having the FLAG sequence was mainly detected as two bands at approximately 5 kDa (the lower diagram, the right lane). However, the β-Alcα was not detected in the immunoprecipitate when the γ-secretase inhibitor L-685,458 was added to the cell culture solution (the lower diagram, the right lane). From this experiment, it was revealed that β-Alcα having the FLAG sequence can be recovered by using the anti-FLAG antibody and it was confirmed that the β-Alcα is a cleavage product of γ-secretase.

(2) Mass Spectrometry of β-Alcα having a FLAG Sequence by MALDI-TOF/MS

HEK293 cells were transfected with an expression vector of AlcαΔE (pcDNA3-FLAG-hAlcαΔE) by using a transfection reagent (LipofectAMINE 2000: Invitrogen) to establish a cell line stably expressing AlcαΔE having the FLAG sequence. The established cell line cells were seeded in a 225-cm² flask. When the cells became confluent, the culture solution was changed to 40 ml of DMEM medium (D5796: Sigma) containing 10% fetal bovine serum and the cells were incubated in a $CO_2$ incubator for 24 hrs. Hereat, 1 μl of a DMSO solution containing 1 mM γ-secretase inhibitor L-685,458 (Calbiochem) was added to 1 ml of the culture medium. As a control, cells to which only the DMSO solution was added were also prepared. The each culture medium was recovered and centrifuged (10000×g, 5 min, high-speed refrigerated centrifuge: Beckmann). An enzyme inhibition solution (a DMSO solution containing 5 mg/ml leupeptin, 5 mg/ml pepstatin A, and 5 mg/ml chymostatin) at a volume ratio of 1/1000 and 10% sodium azide solution at a volume ratio of 1/1000 were added to the resulting supernatant to prepare a sample for immunoprecipitation. Twenty milliliters of this sample was mixed with 20 μl agarose beads (A2220: Sigma) conjugated to 50% (v/v) anti-FLAG antibody (M2) by inverting in a low-temperature chamber (4° C.) overnight (about 12 hrs) for an antigen-antibody reaction. After the reaction, the beads were precipitated and recovered by centrifugation (3000 rpm, 5 min, 4° C., low-speed refrigerated centrifuge: Beckmann).

The recovered beads were washed, in order to eliminate non-specific binding, with 800 μl of washing buffer 1 (0.1% N-octylglucoside, 140 mM NaCl, 10 mM Tris-HCl of pH 8.0, and 0.025% sodium azide) twice and washing buffer 2 (10 mM Tris-HCl of pH 8.0 and 0.025% sodium azide) twice, sequentially. Then, the beads were stirred with 10 μl of a matrix solution (trifluoroacetate (Wako Pure Chemical Industries, Ltd.)/acetonitrile (Sigma)/water (1:20:20) saturated with sinapinic acid (Applied Biosystem)) to elute components from the beads. In order to completely remove the beads, the eluted components were loaded onto a spin column (Amersham Bioscience) and centrifuged to separate the eluted components only. Two microliters of the eluted components were loaded onto a sample plate (Applied Biosystems) and dried, and then analyzed by using a MALDI-TOF/MS (PerSpective Biosystems).

Figure 14:
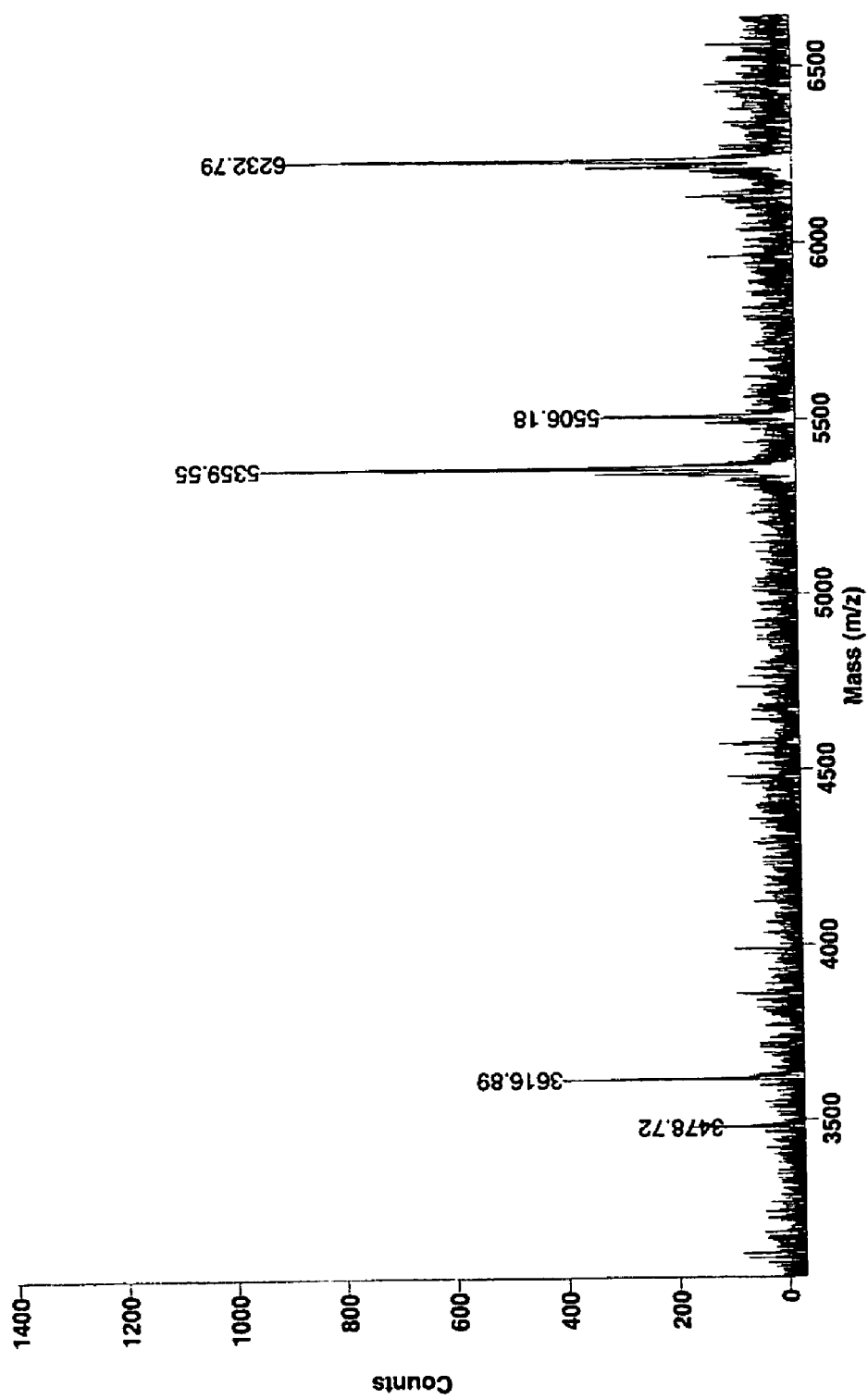
FIG. 14 is a diagram showing the result of mass spectrometry of β-Alcα secreted from cells expressing AlcαΔ.

Signals of the cell-culture solution of the cells not expressing AlcαΔE were used as a background. Peptides having molecular weights of 3619.96, 5359.85, 5507.02, and 6233.83 were detected as β-Alcα having a FLAG sequence (FIG. 14).

Figure 15:
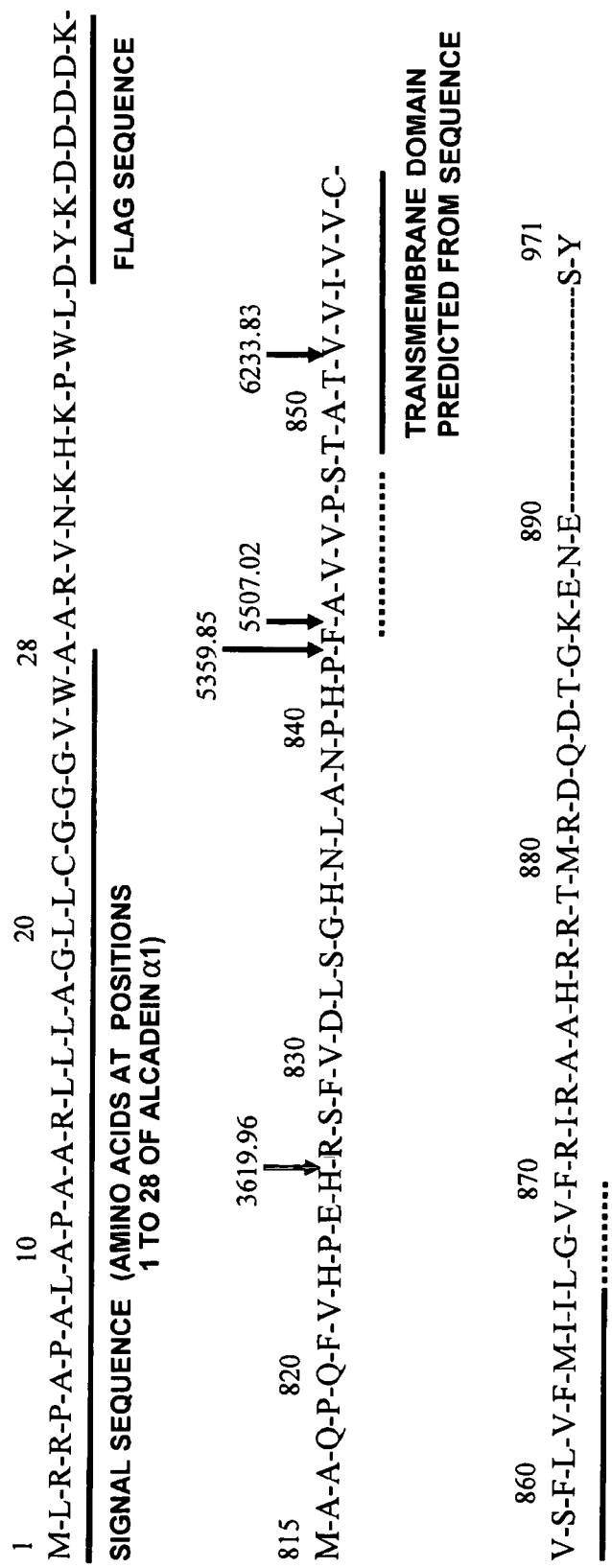
FIG. 15 (SEQ ID NO: 1) is a diagram showing a secondary cleavage site of Alcα determined by the MALDI-TOF/MS method.

Cleavage sites corresponding to these molecular weights were indicated by arrows in FIG. 15. An amino acid sequence predicted to be a transmembrane domain is shown by a solid line and a potential region to be included in the transmembrane domain is shown by a dotted line. On the basis of the fact that cleavage sites determined from the molecular weights of 5359.85, 5507.02, and 6233.83 exist in the transmembrane domain or the potential region to be the transmembrane domain, the cleavage sites can be determined to be in a cleavage domain of γ-secretase. On the other hand, since the cleavage site determined from the molecular weight of 3619.96 obviously exists in an extracellular domain, there is a high possibility that a cleavage product of β-Alcα is generated by the cleavage at the γ-site. Therefore, the secondary cleavage sites of Alcα by γ-secretase are at least three. This agrees with that fact that APP has a plurality of γ-sites and the variety of Aβ is produced and secreted (FIG. 16).

Example 10

Figure 16:
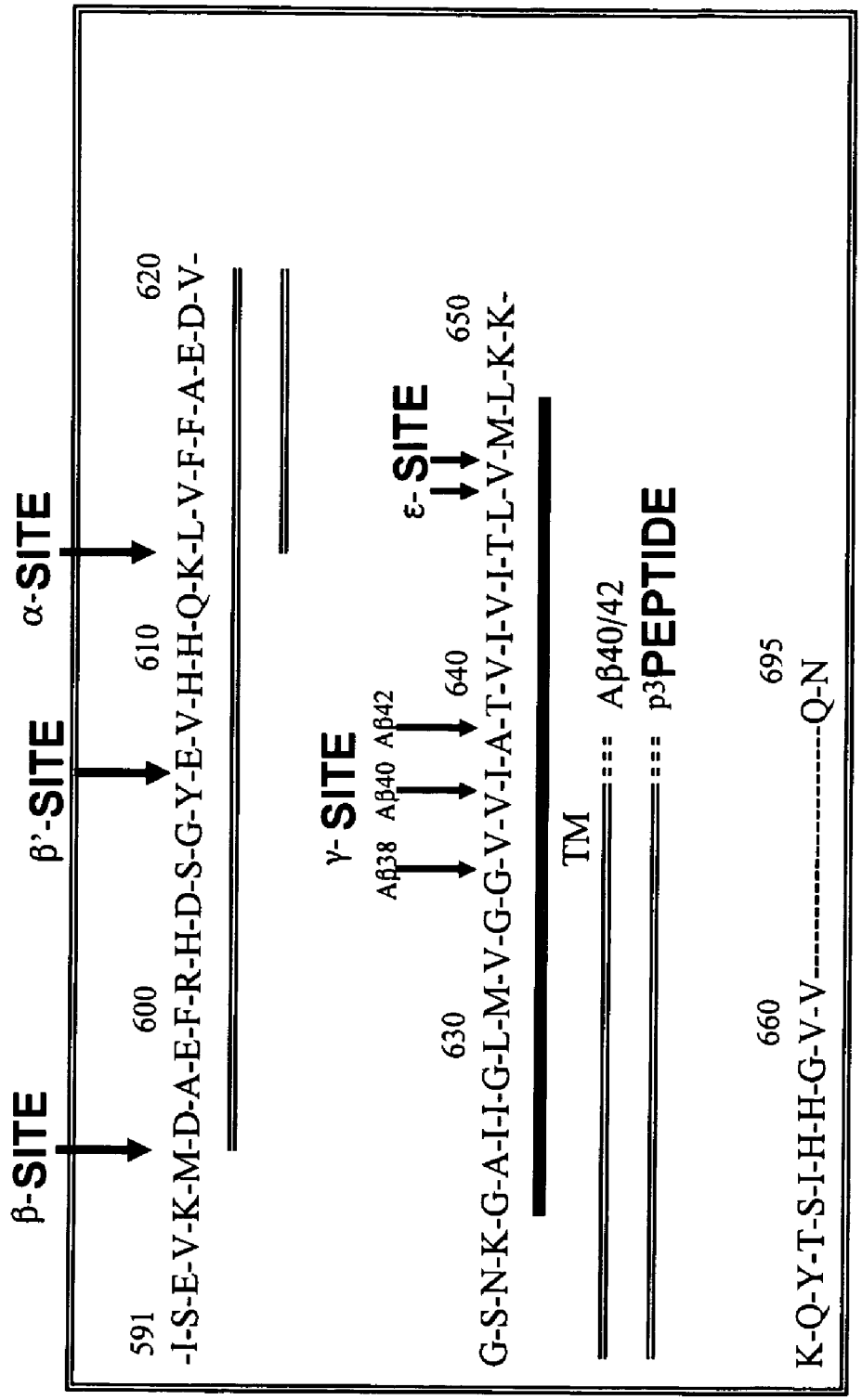
FIG. 16 (SEQ ID NO: 13) is a diagram showing a cleavage site of human APP695.

FIG. 16 shows cleavage sites of APP (human APP695) and cleavage products obtained by the cleavage which have been already revealed (the numbers shown in the Figure are amino acid Nos. in the human APP695 isoform). Examples of the cleavage sites include the α-site and β-site which are primary cleavage sites, the γ-site which is a secondary cleavage site, and the ε-site which was identified recently (Gu, Y., Misonou, H., Sato, T., Dohmae, N., Takio, K., and Ihara, Y. J. Biol. Chem. 2002, 276, 35235-35238). Examples of the cleavage products include Aβ40 and Aβ42 which are main Aβ species and p3 peptide which is a cleavage product of the α-site.

Since Alcα has various similarities to APP, there is a high possibility that Alcα also has a plurality of primary cleavage sites. Hence, the primary cleavage site was identified by determining an amino acid sequence of the N-terminal of a C-terminal fragment (CTF) obtained by the primary cleavage of Alcα. However, since the CTF tends to subsequently receive a secondary cleavage, it is difficult to recover a sufficient amount of the protein for determining its N-terminal sequence from the cell extract. Therefore, a cell line of HEK293 cells stably expressing a dominant-negative protein so that a CTF obtained from Alcα does not receive a secondary cleavage was established by inducing a variant into an active site of presenilin (PS) which is a catalytic subunit of γ-secretase. The cell line was further transfected with an expression vector of Alcα1-FLAG which is Alcα having a FLAG tag at the C-terminal (pcDNA3-hAlcα1-FLAG) by using a transfection reagent (LipofectAMINE 2000: Invitrogen) to establish a cell line stably expressing Alcα1-FLAG.

From the extract of this cell line, CTFα1-FLAG obtained by a primary cleavage was immunoprecipitated. The precipitate was separated by discontinuous SDS electrophoresis with 8% (upper gel)-15% (lower gel) of acrylamide gels and transferred on a PVDF membrane (Immunobilon-PSQ: Millipore). The CTFα1-FLAG was detected by Coomassie brilliant blue staining. Two kinds of protein of approximately 30 kDa, which were detected by antibody-specific detection, were analyzed by a gas-phase protein sequencer to determine three amino acid sequences derived from Alcα1. The details will now be described.

HEK293 cells were transfected with an expression vector (pcDNA3-PS1D385A) of a PS1 (D385A) variant protein obtained by substituting alanine for aspartic acid at position 385 in presenilin 1 (PS1) by using a transfection reagent (LipofectAMINE 2000: Invitrogen); thus, a cell line stably expressing PS1 (D385A) was established. The cells of this cell line were further transfected with an AlcαFLAG expression vector (pcDNA3-hAlcα1-FLAG) by using a transfection reagent (LipofectAMINE 2000: Invitrogen).

Figure 17:
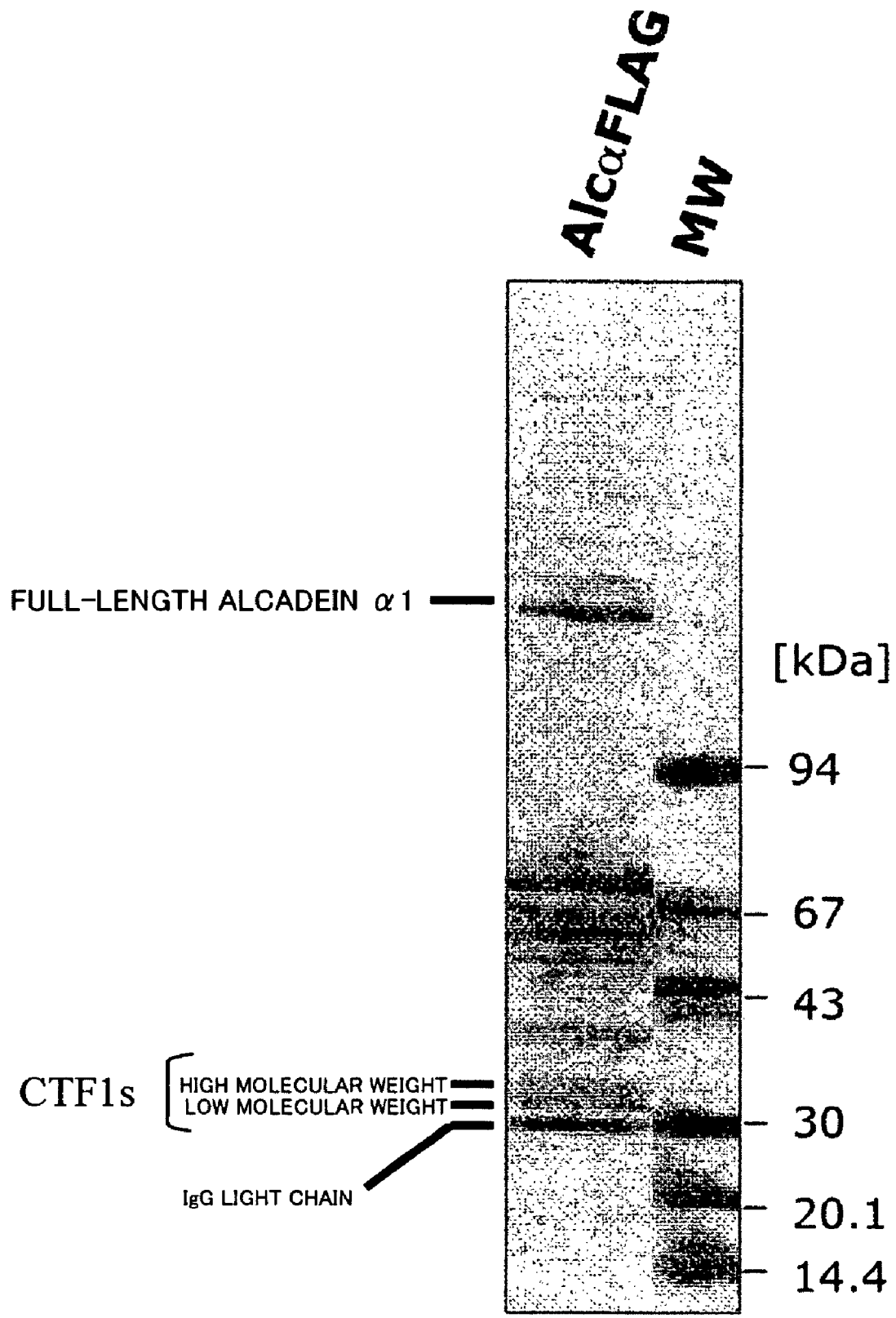
FIG. 17 is a diagram showing the results of electrophoresis of a C-terminal region obtained by a primary cleavage of Alcα1.

The cells of this cell line (denoted as hAlcα1 FLAG/PS1D385A-293cell) were incubated in four 10-cm dishes until reaching a confluent state (about $1\times10^8$ cells/dish). The cells were washed with ice-cooled PBS. Then, 15 ml of an HBST solution (10 mM HEPES of pH 7.4, 150 mM NaCl, and 0.5% Triton X-100) containing an enzyme inhibition solution (a DMSO solution containing 5 μg/ml leupeptin, 5 μg/ml pepstatin A, and 5 μg/ml chymostatin) was added to the cells and the resulting mixture was stirred by inverting at 4° C. for 0.5 hrs to solubilize the cells. The solubilized cells were centrifuged (12000×g, 10 min, 4° C., high-speed microcentrifuge: TOMY SEIKO CO., LTD.); thus, soluble components were recovered as the supernatant. Fifteen milliliters of the solubilized components was mixed with 30 μl of agarose beads (A2220: Sigma) conjugated to 50% (v/v) anti-FLAG antibody (M2) by inverting in a low-temperature chamber (4° C.) overnight (about 12 hrs) for an antigen-antibody reaction. After the reaction, the beads were precipitated and recovered by centrifugation (3000 rpm, 5 min, 4° C., low-speed refrigerated centrifuge: Beckmann). Then, the beads were washed with 1 ml of HBST 3 times. After the addition of 2 mg/ml FLAG-peptide-containing HBST (30 μl), the immunoprecipitate was competitively eluted; which is a method for performing antigen elution under moderate conditions in order to avoid contamination of immunoglobulin light chains (30 kDa or less) because the molecular weight of CTF1 of Alcα is about 30 kDa. The eluate was centrifuged (12000×g, 10 min, 4° C., high-speed microcentrifuge: TOMY SEIKO CO., LTD.). Then, 5×SDS sample buffer was added to the supernatant at a volume ratio of 1/5 and acrylamide gel electrophoresis was performed according to the general method of Laemmili. The separated proteins were transferred on an Immobilon-PSQ membrane (Millipore) and detected by staining using Coomassie brilliant blue (CBB) stain (FIG. 17).

Figure 18:
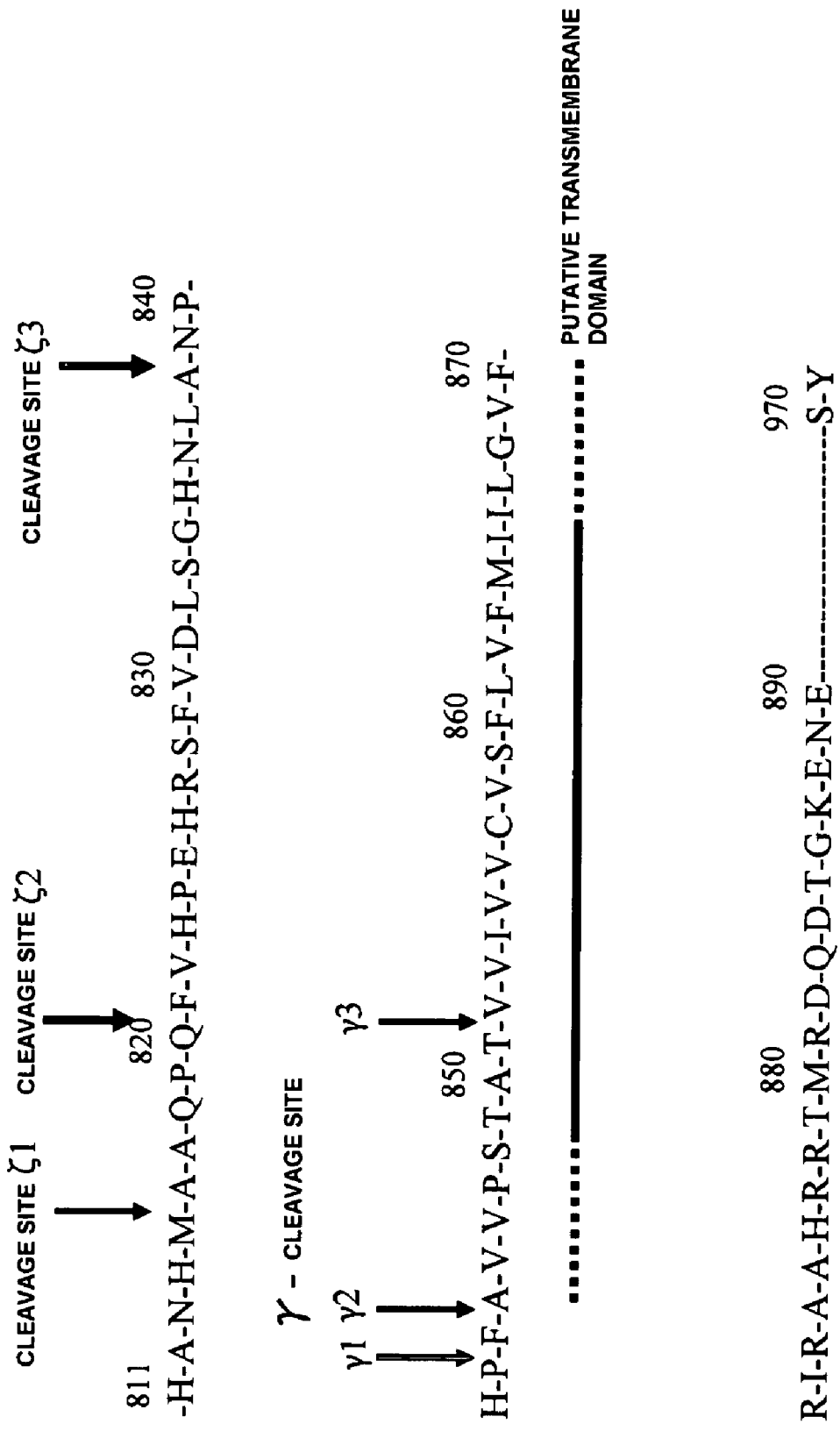
FIG. 18 (SEQ ID NO: 1) is a diagram showing cleavage sites of Alcα.

Two kinds of protein (proteins indicated as CTF1s) were detected at approximately 30 kDa. The amino acid sequences of these proteins were determined by using a gas-phase protein sequencer 492HT (Applied BioSystem). The results revealed that the protein with a higher molecular weight includes two types of amino acid sequence. The primary cleavage sites deduced based on these sequences are between Met-815 and Ala-816 (this cleavage site is referred to as "ζ1") and between Gln-820 and Phe-821 (this cleavage site is referred to as "ζ2") (FIG. 18). The ζ1 agrees with the site determined in Example 8. The ζ2 is a newly found primary cleavage site. Additionally, it was revealed that the protein with a lower molecular weight of CTF1s includes one type of amino acid sequence. The primary cleavage site deduced based on this sequence is between Ala-838 and Asn-839 (this cleavage site is referred to as "ζ3") (311) (FIG. 18).

As shown above, Alcα has 3 primary cleavage sites (ζ1, ζ2, and η3) and 3 secondary cleavage sites (γ1, γ2, and γ3). As a result, it is understood that, in human beings, at least 9 types of β-Alcα are produced (Table 1).

TABLE 1

| PRIMARY CLEAVAGE SITE | SECONDARY CLEAVAGE SITE | THE NUMBER OF AMINO ACIDS | SEQUENCE LISTING |
|---|---|---|---|
| ζ1 | γ1 | 27 | SEQ ID NO: 4 |
| ζ1 | γ2 | 28 | SEQ ID NO: 5 |
| ζ1 | γ3 | 36 | SEQ ID NO: 6 |
| ζ2 | γ1 | 22 | SEQ ID NO: 7 |
| ζ2 | γ2 | 23 | SEQ ID NO: 8 |
| ζ2 | γ3 | 31 | SEQ ID NO: 9 |
| ζ3 | γ1 | 4 | SEQ ID NO: 10 |
| ζ3 | γ2 | 5 | SEQ ID NO: 11 |
| ζ3 | γ3 | 13 | SEQ ID NO: 12 |

The result that a plurality of types of β-Alcα are generated well agrees with the fact that a plurality of types of Aβ generated from APP which is synchronously metabolized.

Example 11

In Alzheimer's disease (AD), it is recognized not only an increase in the generation of Aβ but also a change in the molecular species of Aβ. Furthermore, it is reported that the ratio of the amount of Aβ42, which is highly aggregative, to the total amount of generated Aβ is increased in AD patients. The increase of the ratio of Aβ42 is thought to be highly involved in the onset of Alzheimer's disease. For example, it is known that the ratio of Aβ42 to Aβ is prominently increased in patients of familial Alzheimer's disease (FAD) having a variant in the presenilin gene. Since Alcα has various similarities to APP, there is a possibility in Alcα that the molecular species of β-Alcα generated by a presenilin variant is changed as in APP. Consequently, in order to confirm this possibility, the following experiment was conducted.

Expression vectors (pcDNA3-PS1I143F, pcDNA3-PS1R278T, pcDNA3-PS1A434C, and pcDNA3-PS1L435F) expressing four types of PS1 variant found in AD patients, i.e., I143F (substituting Phe for Ile at position 143), R278T (substituting Thr for Arg at position 278), A434C (substituting Cys for Ala at position 434), and L435F (substituting Phe for Leu at position 435) were prepared. These vectors and an expression vector of C99/CTF of APP (pcDNA3-APPC99) were introduced to HEK293 cells by using a transfection reagent (LipofectAMINE 2000: Invitrogen) to establish a cell line stably expressing both proteins. The cells of the cell line were seeded in a 10-cm dish (Corning). When the cells became confluent, pcDNA3-FLAG-hAlcαΔE was introduced into the cells by using a transfection reagent (LipofectAMINE 2000: Invitrogen) to transitorily express CTF1 of Alcadein α.

Separately, expression vectors (pcDNA3-PS1 and pcDNA3-PS1D385A) expressing wild-type PS1 (wt) and inactive-type PS1 (D385A, Asp at the catalytic site of PS1 is substituted with Ala not to have γ-secretase activity) were prepared and introduced into HEK293 cells by using a transfection reagent (LipofectAMINE 2000: Invitrogen) to establish cell lines stably expressing both types of PS1. The cells of each cell line were seeded in a 10-cm dish (Corning). When the cells became confluent, pcDNA3-APPC99 and pcDNA3-FLAG-hAlcαΔE were introduced into the cells by using a transfection reagent (LipofectAMINE 2000: Invitrogen) to transitorily express CTF of APP and CTF1 of Alcadein α.

The cells transfected with genes were incubated in a CO$_2$ incubator for 24 hrs. The culture solution was recovered and centrifuged (15000 rpm, 5 min, 4° C., high-speed refrigerated centrifuge: Beckmann). To 7.5 ml of the supernatant, 7.5 µl of an enzyme inhibition solution (a DMSO solution containing 5 mg/ml leupeptin, 5 mg/ml pepstatin A, and 5 mg/ml chymostatin) was added to prepare a sample. After the addition of 6 µl of an anti-FLAG antibody solution (M2: Sigma, lot No. 103k6043) to the sample, the resulting mixture was mixed by inverting at 4° C. for 1 hr. Then, 50 µl of rinse buffer containing 25% protein G-sepharose was added and the mixture was mixed by inverting at 4° C. overnight for an antigen-antibody reaction. After the reaction, the beads were washed with washing buffer 1 (1 M NaCl, 20 mM Tris-HCl of pH 7.4, and 0.1% Triton X-100), washing buffer 2 (150 mM NaCl, 5 mM EDTA, 50 mM Tris-HCl of pH 7.4, 1% Triton X-100, and 0.05% SDS), and rinse buffer (10 mM Tris-HCl of pH 7.4, 1 mM EDTA, 0.1% Triton X-100, and 150 mM NaCl), sequentially. Then, 20 µl of a sample-buffer mixture (a mixture of 10 µl of 2×SDS sample buffer and 10 µl of 8 M urea solution) was added to the beads and stirred. The beads were boiled for 5 min to elute components which were adsorbed to the beads.

Figure 19:
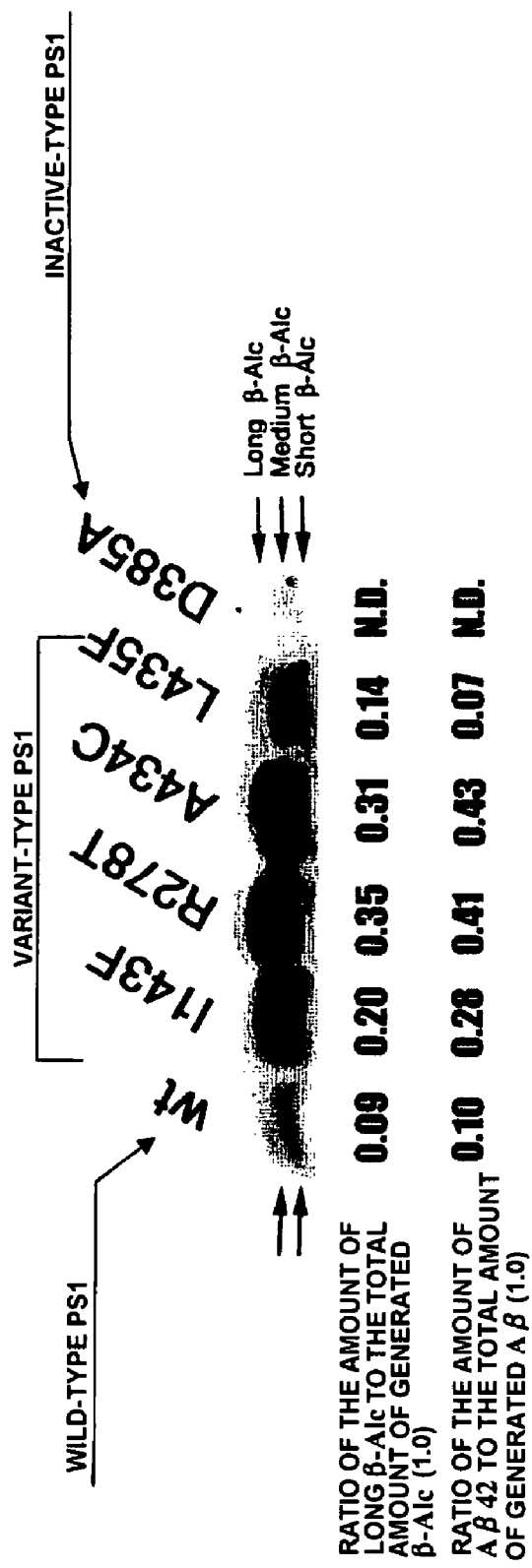
FIG. 19 is a diagram showing the results of Western blotting of cells expressing various PS1 variants and AlcαΔE.

After the centrifugation, the supernatant components were separated by 20% acrylamide Tris-Tricine gel electrophoresis and then subjected to Western blotting using an anti-FLAG antibody solution (M2: Sigma). The reacted β-Alcα having a FLAG tag was detected by using an ECL kit (Pharmacia) and quantitatively determined by using an NIH image software. At the same time, Aα40 and Aβ42 in the culture medium were quantitatively determined by sELISA according to the method of Tomita, et al. (J. Biol. Chem. 1988, 273, 6277-6284). FIG. 19 shows the results of the Western blotting and ratios of the amount of long β-Alcα to the total amount of generated β-Alcα (1.0) and ratios of the amount of AP42 to the total amount of generated Aβ (1.0). The N.D. in the Figure means the value was lower than the detection limit.

In the cells expressing the wild-type PS1, 2 types of β-Alc (indicated as short β-Alc and medium β-Alc in the Figure) were mainly detected. On the other hand, in the cells expressing PS1 having a FAD variant, the amount of β-Alc (indicated as long β-Alc) having a higher molecular weight was increased. The ratio of the long β-Alc to the total β-Alcα was increased in the cells expressing a PS1 variant; which is the same tendency as the increase in the ratio of Aβ42 to the total Aβ. Namely, it was revealed that a qualitative change in β-Alc reflects a quantitative change in Aβ. A qualitative change in β-Alc (such as the increase in the ratio of long β-Alc) in cerebrospinal fluid or blood of patients reflects a qualitative change in Aβ. Therefore, the detection of β-Alc instead of the detection of Aβ42, which is highly aggregative, can find patients at an early stage or pre-patients of whom qualitative change is difficult to detect.

Example 12

Figure 20:
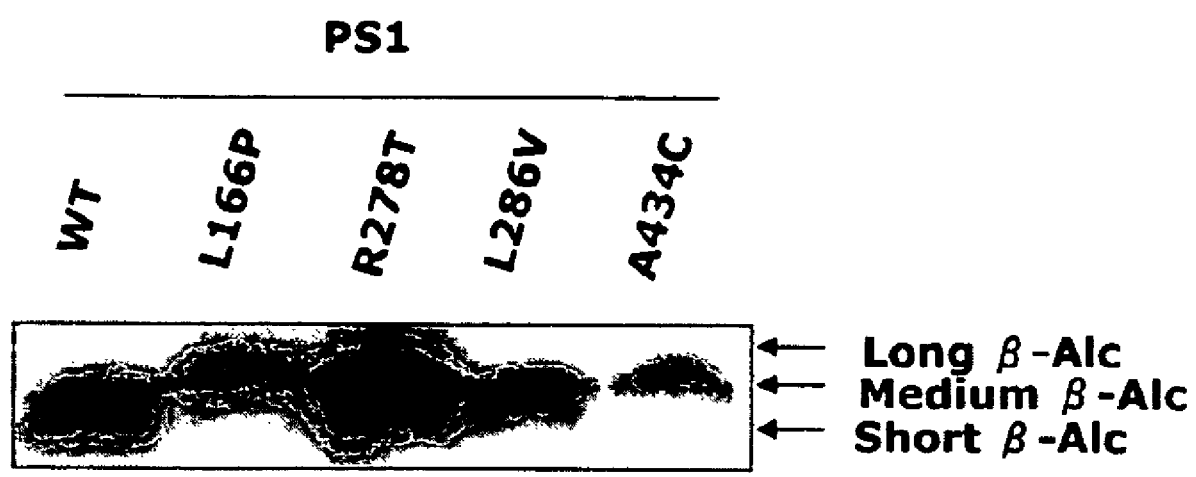
FIG. 20 is a diagram showing the results of Western blotting of cells expressing various PS1 variants (including L166P variant-type PS1) and AlcαΔE.
Figure 21:
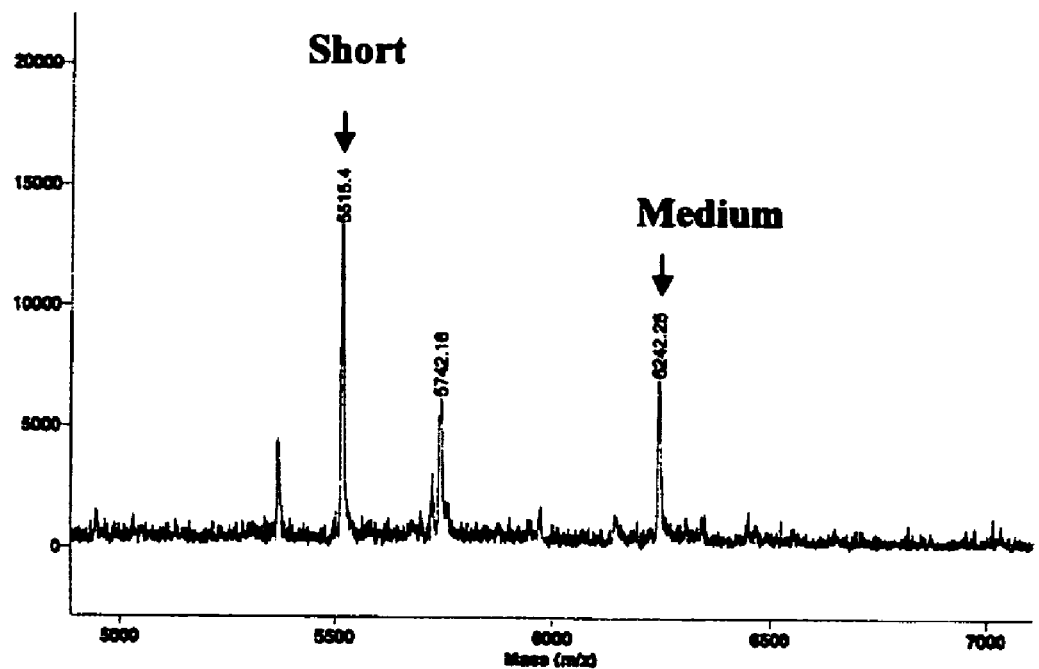
FIG. 21 is diagrams showing the results of mass spectrometry of β-Alc obtained from wild-type PS1 or L166P variant-type PS1.
Figure 21:
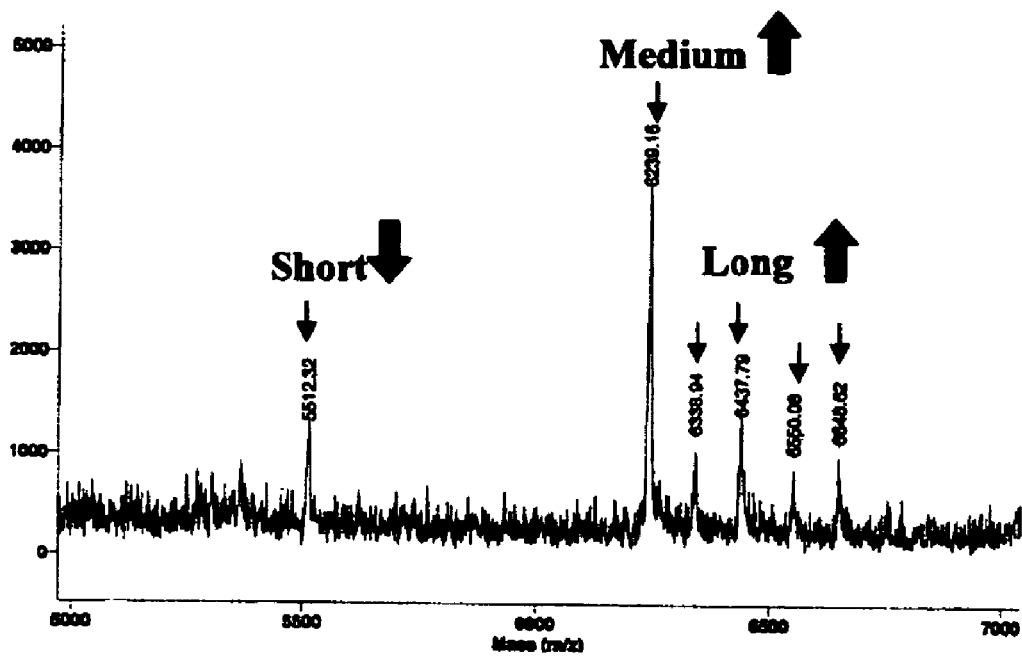

In order to use in the determination of a cleavage site at the C-terminal of β-Alc shown in FIG. 19 by using a MALDI-TOF/MS, a PS1 variant expressing a larger amount of a high-molecular-weight β-Alc was intensively searched by conducting the same experiment as in Example 11. As a result, as shown in FIG. 20, it was found that a large amount of high-molecular-weight β-Alc was secreted in the culture medium of the cells expressing L166P (Leu at position 166 is substituted with Pro) PS1 variant, compared with other PS1 variants. Consequently, the molecular weights of β-Alc produced and secreted by the wild-type PS1 and the L166P variant-type PS1 were determined by mass spectrometry according to the method in Example 9. FIG. 21 shows the results. In the cells expressing the L166P variant-type PS1, the amount of short β-Alc (indicated by a bold downward arrow) is decreased and the amount of medium β-Alc (indicated by a bold upward arrow) is increased compared to those in the cells expressing the wild-type PS1. This is also obvious from the results of the Western blotting analysis shown in FIG. 20. Furthermore, long β-Alc, which was not detected in the cells expressing the wild-type PS1, was also detected.

Figure 22:
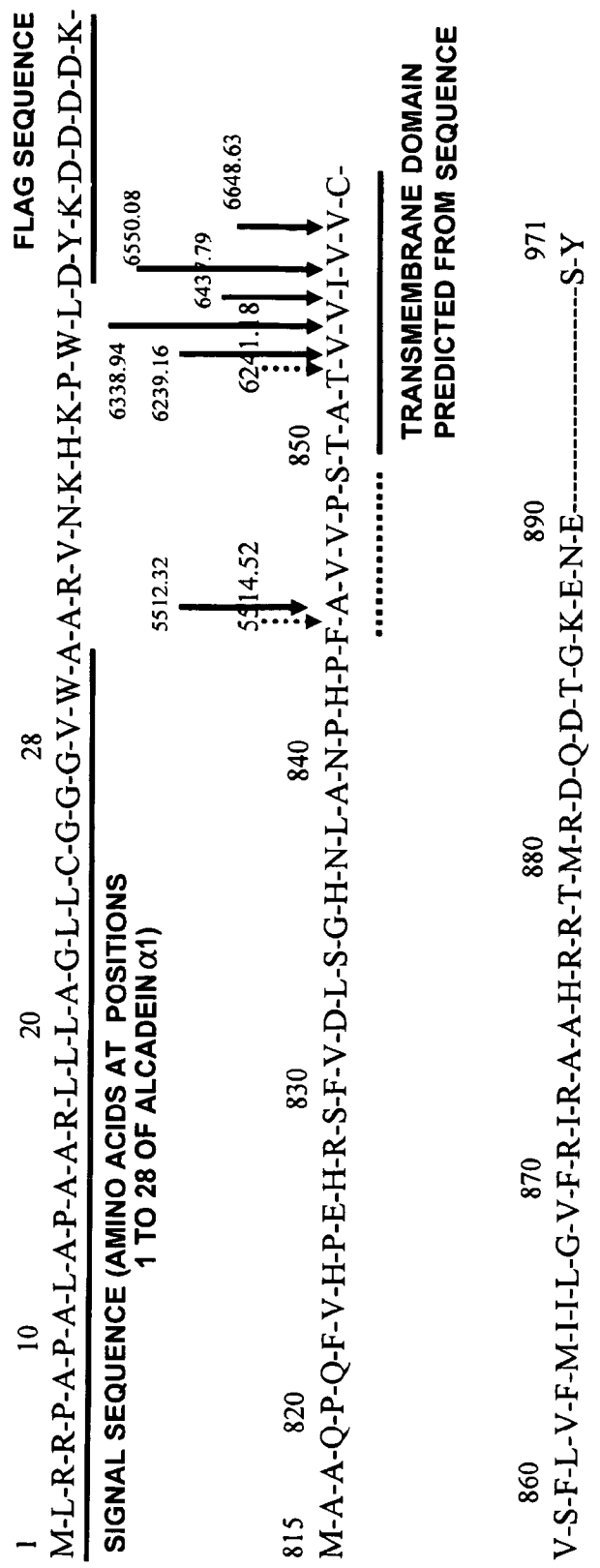
FIG. 22 (SEQ ID NO: 1) is a diagram showing cleavage sites of β-Alc.
Figure 23:
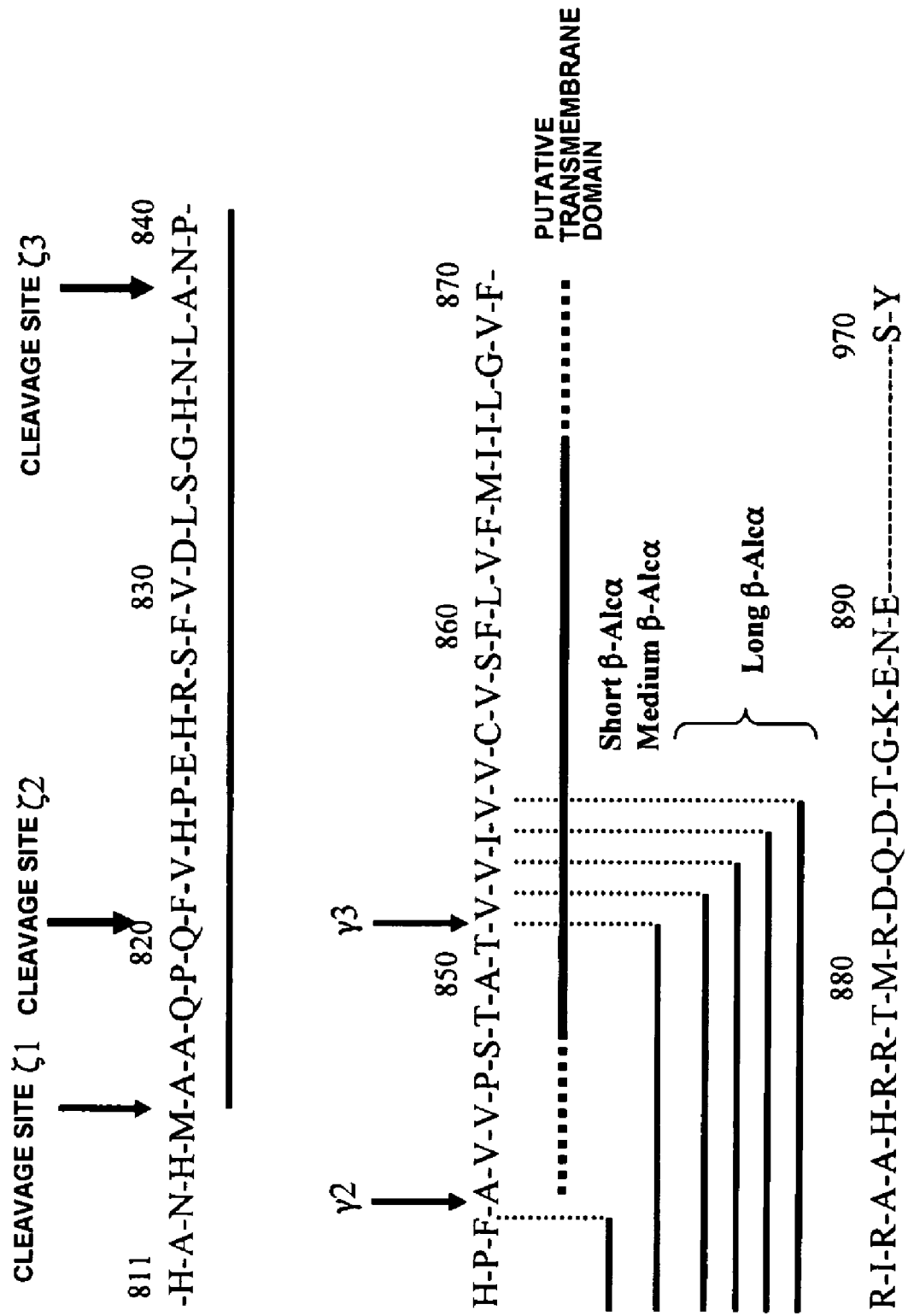
FIG. 23 (SEQ ID NO: 1) is a diagram schematically showing molecular species of β-Alc.

FIG. 22 shows the cleavage sites of β-Alc which were revealed from the results shown in FIG. 21. The dotted line arrows indicate the cleavage sites in the cells expressing the wild-type PS1 and the solid line arrows indicate the cleavage sites in the cells expressing the L166P variant-type PS1. It was revealed that the cleavage sites of β-Alc shifted to the C-terminal side in the L166P variant-type PS1. This result well agrees with the fact that the cleavage site at the C-terminal side of Aβ shifts to the C-terminal side in a variant-type PS1 of familial Alzheimer's disease. FIG. 23 schematically shows 3 cleavage sites (ζ1, ζ2, and ζ3) at the N-terminal side and 3 cleavage sites (γ1, γ2, and γ3) at the C-terminal side of β-Alc and β-Alc molecular species generated by the cleavage at the γ-site shifted to the C-terminal side by the variant-type PS1 (the cleavage site γ1 was not detected in the experiment in Example 12).

The present invention contains subject matter disclosed in the specification and/or the drawings of Japanese Patent Application No. 2003-375363 on which the claim for a priority right is based, and the entire contents of the documents, patents, and patent applications cited as references are incorporated herein by reference.

The invention claimed is:

1. An isolated peptide consisting of the amino acid sequence selected from the group consisting of SEQ ID NOS: 4 to 12 and 14 to 17.

2. A method for diagnosing Alzheimer's disease, comprising:

obtaining a sample of brain tissue taken from a subject, determining co-localization of the peptide according to claim 1 with amyloid precursor protein (APP) present in said sample, wherein Alzheimer's disease is indicated when the co-localization is detected as compared to the absence of said co-localization in a control non-Alzheimer's disease sample.

* * * * *

SEQUENCE LISTING

<160> NUMBER OF SEQ ID NOS: 17

<210> SEQ ID NO 1
<211> LENGTH: 971
<212> TYPE: PRT
<213> ORGANISM: human

<400> SEQUENCE: 1

Met Leu Arg Arg Pro Ala Pro Ala Leu Ala Pro Ala Ala Arg Leu Leu
1               5                   10                  15

Leu Ala Gly Leu Leu Cys Gly Gly Val Trp Ala Ala Arg Val Asn
                20                  25                  30

Lys His Lys Pro Trp Leu Glu Pro Thr Tyr His Gly Ile Val Thr Glu
            35                  40                  45

Asn Asp Asn Thr Val Leu Leu Asp Pro Pro Leu Ile Ala Leu Asp Lys
    50                  55                  60

Asp Ala Pro Leu Arg Phe Ala Gly Glu Ile Cys Gly Phe Lys Ile His
65                  70                  75                  80

Gly Gln Asn Val Pro Phe Asp Ala Val Val Asp Lys Ser Thr Gly
                85                  90                  95

Glu Gly Val Ile Arg Ser Lys Glu Lys Leu Asp Cys Glu Leu Gln Lys
                100                 105                 110

Asp Tyr Ser Phe Thr Ile Gln Ala Tyr Asp Cys Gly Lys Gly Pro Asp
            115                 120                 125

Gly Thr Asn Val Lys Lys Ser His Lys Ala Thr Val His Ile Gln Val
        130                 135                 140

Asn Asp Val Asn Glu Tyr Ala Pro Val Phe Lys Glu Lys Ser Tyr Lys
145                 150                 155                 160

Ala Thr Val Ile Glu Gly Lys Gln Tyr Asp Ser Ile Leu Arg Val Glu
                165                 170                 175

Ala Val Asp Ala Asp Cys Ser Pro Gln Phe Ser Gln Ile Cys Ser Tyr
            180                 185                 190

Glu Ile Ile Thr Pro Asp Val Pro Phe Thr Val Asp Lys Asp Gly Tyr
        195                 200                 205

Ile Lys Asn Thr Glu Lys Leu Asn Tyr Gly Lys Glu His Gln Tyr Lys
    210                 215                 220

Leu Thr Val Thr Ala Tyr Asp Cys Gly Lys Lys Arg Ala Thr Glu Asp
225                 230                 235                 240

Val Leu Val Lys Ile Ser Ile Lys Pro Thr Cys Thr Pro Gly Trp Gln
                245                 250                 255

-continued

```
Gly Trp Asn Asn Arg Ile Glu Tyr Glu Pro Gly Thr Gly Ala Leu Ala
            260                 265                 270

Val Phe Pro Asn Ile His Leu Glu Thr Cys Asp Glu Pro Val Ala Ser
        275                 280                 285

Val Gln Ala Thr Val Glu Leu Glu Thr Ser His Ile Gly Lys Gly Cys
    290                 295                 300

Asp Arg Asp Thr Tyr Ser Glu Lys Ser Leu His Arg Leu Cys Gly Ala
305                 310                 315                 320

Ala Ala Gly Thr Ala Glu Leu Leu Pro Ser Pro Ser Gly Ser Leu Asn
                325                 330                 335

Trp Thr Met Gly Leu Pro Thr Asp Asn Gly His Asp Ser Asp Gln Val
            340                 345                 350

Phe Glu Phe Asn Gly Thr Gln Ala Val Arg Ile Pro Asp Gly Val Val
        355                 360                 365

Ser Val Ser Pro Lys Glu Pro Phe Thr Ile Ser Val Trp Met Arg His
    370                 375                 380

Gly Pro Phe Gly Arg Lys Lys Glu Thr Ile Leu Cys Ser Ser Asp Lys
385                 390                 395                 400

Thr Asp Met Asn Arg His His Tyr Ser Leu Tyr Val His Gly Cys Arg
                405                 410                 415

Leu Ile Phe Leu Phe Arg Gln Asp Pro Ser Glu Glu Lys Lys Tyr Arg
            420                 425                 430

Pro Ala Glu Phe His Trp Lys Leu Asn Gln Val Cys Asp Glu Glu Trp
        435                 440                 445

His His Tyr Val Leu Asn Val Glu Phe Pro Ser Val Thr Leu Tyr Val
    450                 455                 460

Asp Gly Thr Ser His Glu Pro Phe Ser Val Thr Glu Asp Tyr Pro Leu
465                 470                 475                 480

His Pro Ser Lys Ile Glu Thr Gln Leu Val Val Gly Ala Cys Trp Gln
                485                 490                 495

Glu Phe Ser Gly Val Glu Asn Asp Asn Glu Thr Glu Pro Val Thr Val
            500                 505                 510

Ala Ser Ala Gly Gly Asp Leu His Met Thr Gln Phe Phe Arg Gly Asn
        515                 520                 525

Leu Ala Gly Leu Thr Leu Arg Ser Gly Lys Leu Ala Asp Lys Lys Val
    530                 535                 540

Ile Asp Cys Leu Tyr Thr Cys Lys Glu Gly Leu Asp Leu Gln Val Leu
545                 550                 555                 560

Glu Asp Ser Gly Arg Gly Val Gln Ile Gln Ala His Pro Ser Gln Leu
                565                 570                 575

Val Leu Thr Leu Glu Gly Glu Asp Leu Gly Glu Leu Asp Lys Ala Met
            580                 585                 590

Gln His Ile Ser Tyr Leu Asn Ser Arg Gln Phe Pro Thr Pro Gly Ile
        595                 600                 605

Arg Arg Leu Lys Ile Thr Ser Thr Ile Lys Cys Phe Asn Glu Ala Thr
    610                 615                 620

Cys Ile Ser Val Pro Pro Val Asp Gly Tyr Val Met Val Leu Gln Pro
625                 630                 635                 640

Glu Glu Pro Lys Ile Ser Leu Ser Gly Val His His Phe Ala Arg Ala
                645                 650                 655

Ala Ser Glu Phe Glu Ser Ser Glu Gly Val Phe Leu Phe Pro Glu Leu
            660                 665                 670
```

```
Arg Ile Ile Ser Thr Ile Thr Arg Glu Val Glu Pro Glu Gly Asp Gly
            675                 680                 685

Ala Glu Asp Pro Thr Val Gln Glu Ser Leu Val Ser Glu Glu Ile Val
        690                 695                 700

His Asp Leu Asp Thr Cys Glu Val Thr Val Glu Gly Glu Glu Leu Asn
705                 710                 715                 720

His Glu Gln Glu Ser Leu Glu Val Asp Met Ala Arg Leu Gln Gln Lys
                725                 730                 735

Gly Ile Glu Val Ser Ser Ser Glu Leu Gly Met Thr Phe Thr Gly Val
            740                 745                 750

Asp Thr Met Ala Ser Tyr Glu Val Leu His Leu Leu Arg Tyr Arg
        755                 760                 765

Asn Trp His Ala Arg Ser Leu Leu Asp Arg Lys Phe Lys Leu Ile Cys
        770                 775                 780

Ser Glu Leu Asn Gly Arg Tyr Ile Ser Asn Glu Phe Lys Val Glu Val
785                 790                 795                 800

Asn Val Ile His Thr Ala Asn Pro Met Glu His Ala Asn His Met Ala
                805                 810                 815

Ala Gln Pro Gln Phe Val His Pro Glu His Arg Ser Phe Val Asp Leu
            820                 825                 830

Ser Gly His Asn Leu Ala Asn Pro His Pro Phe Ala Val Val Pro Ser
        835                 840                 845

Thr Ala Thr Val Val Ile Val Val Cys Val Ser Phe Leu Val Phe Met
850                 855                 860

Ile Ile Leu Gly Val Phe Arg Ile Arg Ala Ala His Arg Arg Thr Met
865                 870                 875                 880

Arg Asp Gln Asp Thr Gly Lys Glu Asn Glu Met Asp Trp Asp Asp Ser
                885                 890                 895

Ala Leu Thr Ile Thr Val Asn Pro Met Glu Thr Tyr Glu Asp Gln His
            900                 905                 910

Ser Ser Glu Glu Glu Glu Glu Glu Glu Glu Ser Glu Asp
        915                 920                 925

Gly Glu Glu Glu Asp Asp Ile Thr Ser Ala Glu Ser Glu Ser Ser Glu
930                 935                 940

Glu Glu Glu Gly Glu Gln Gly Asp Pro Gln Asn Ala Thr Arg Gln Gln
945                 950                 955                 960

Gln Leu Glu Trp Asp Asp Ser Thr Leu Ser Tyr
            965                 970

<210> SEQ ID NO 2
<211> LENGTH: 968
<212> TYPE: PRT
<213> ORGANISM: human

<400> SEQUENCE: 2

Met Val Leu Gly Cys Glu Leu Ser Gly Ser Thr Arg Val Val Val Gly
1               5                   10                  15

Val Glu Ala Leu Leu Thr Gly Ala Ser Ser Pro Leu Pro Gly Val Gly
            20                  25                  30

Pro Ala Asn Lys His Lys Pro Trp Ile Glu Ala Glu Tyr Gln Gly Ile
        35                  40                  45

Val Met Glu Asn Asp Asn Thr Val Leu Leu Asn Pro Pro Leu Phe Ala
    50                  55                  60

Leu Asp Lys Asp Ala Pro Leu Arg Tyr Ala Gly Glu Ile Cys Gly Phe
65                  70                  75                  80
```

```
Arg Leu His Gly Ser Gly Val Pro Phe Glu Ala Val Ile Leu Asp Lys
                85                  90                  95
Ala Thr Gly Glu Gly Leu Ile Arg Ala Lys Glu Pro Val Asp Cys Glu
            100                 105                 110
Ala Gln Lys Glu His Thr Phe Thr Ile Gln Ala Tyr Asp Cys Gly Glu
            115                 120                 125
Gly Pro Asp Gly Ala Asn Thr Lys Lys Ser His Lys Ala Thr Val His
        130                 135                 140
Val Arg Val Asn Asp Val Asn Glu Phe Ala Pro Val Phe Val Glu Arg
145                 150                 155                 160
Leu Tyr Arg Ala Ala Val Thr Glu Gly Lys Leu Tyr Asp Arg Ile Leu
                165                 170                 175
Arg Val Glu Ala Ile Asp Gly Asp Cys Ser Pro Gln Tyr Ser Gln Ile
            180                 185                 190
Cys Tyr Tyr Glu Ile Leu Thr Pro Asn Thr Pro Phe Leu Ile Asp Asn
            195                 200                 205
Asp Gly Asn Ile Glu Asn Thr Glu Lys Leu Gln Tyr Ser Gly Glu Arg
        210                 215                 220
Leu Tyr Lys Phe Thr Val Thr Ala Tyr Asp Cys Gly Lys Lys Arg Ala
225                 230                 235                 240
Ala Asp Asp Ala Glu Val Glu Ile Gln Val Lys Pro Thr Cys Lys Pro
                245                 250                 255
Ser Trp Gln Gly Trp Asn Lys Arg Ile Glu Tyr Ala Pro Gly Ala Gly
            260                 265                 270
Ser Leu Ala Leu Phe Pro Gly Ile Arg Leu Glu Thr Cys Asp Glu Pro
            275                 280                 285
Leu Trp Asn Ile Gln Ala Thr Ile Glu Leu Gln Thr Ser His Val Ala
        290                 295                 300
Lys Gly Cys Asp Arg Asp Asn Tyr Ser Glu Arg Ala Leu Arg Lys Leu
305                 310                 315                 320
Cys Gly Ala Ala Thr Gly Glu Val Asp Leu Leu Pro Met Pro Gly Pro
                325                 330                 335
Asn Ala Asn Trp Thr Ala Gly Leu Ser Val His Tyr Ser Gln Asp Ser
            340                 345                 350
Ser Leu Ile Tyr Trp Phe Asn Gly Thr Gln Ala Val Gln Val Pro Leu
            355                 360                 365
Gly Gly Pro Ser Gly Leu Gly Ser Gly Pro Gln Asp Ser Leu Ser Asp
        370                 375                 380
His Phe Thr Leu Ser Phe Trp Met Lys His Gly Val Thr Pro Asn Lys
385                 390                 395                 400
Gly Lys Lys Glu Glu Thr Ile Val Cys Asn Thr Val Gln Asn Glu
                405                 410                 415
Asp Gly Phe Ser His Tyr Ser Leu Thr Val His Gly Cys Arg Ile Ala
            420                 425                 430
Phe Leu Tyr Trp Pro Leu Leu Glu Ser Ala Arg Pro Val Lys Phe Leu
            435                 440                 445
Trp Lys Leu Glu Gln Val Cys Asp Asp Glu Trp His Tyr Ala Leu
        450                 455                 460
Asn Leu Glu Phe Pro Thr Val Thr Leu Tyr Thr Asp Gly Ile Ser Phe
465                 470                 475                 480
Asp Pro Ala Leu Ile His Asp Asn Gly Leu Ile His Pro Pro Arg Arg
                485                 490                 495
```

-continued

```
Glu Pro Ala Leu Met Ile Gly Ala Cys Trp Thr Glu Lys Asn Lys
                500                 505                 510

Glu Lys Glu Lys Gly Asp Asn Ser Thr Asp Thr Thr Gln Gly Asp Pro
            515                 520                 525

Leu Ser Ile His His Tyr Phe His Gly Tyr Leu Ala Gly Phe Ser Val
        530                 535                 540

Arg Ser Gly Arg Leu Glu Ser Arg Glu Val Ile Glu Cys Leu Tyr Ala
545                 550                 555                 560

Cys Arg Glu Gly Leu Asp Tyr Arg Asp Phe Glu Ser Leu Gly Lys Gly
                565                 570                 575

Met Lys Val His Val Asn Pro Ser Gln Ser Leu Leu Thr Leu Glu Gly
            580                 585                 590

Asp Asp Val Glu Thr Phe Asn His Ala Leu Gln His Val Ala Tyr Met
        595                 600                 605

Asn Thr Leu Arg Phe Ala Thr Pro Gly Val Arg Pro Leu Arg Leu Thr
    610                 615                 620

Thr Ala Val Lys Cys Phe Ser Glu Glu Ser Cys Val Ser Ile Pro Glu
625                 630                 635                 640

Val Glu Gly Tyr Val Val Leu Gln Pro Asp Ala Pro Gln Ile Leu
                645                 650                 655

Leu Ser Gly Thr Ala His Phe Ala Arg Pro Ala Val Asp Phe Glu Gly
            660                 665                 670

Thr Asn Gly Val Pro Leu Phe Pro Asp Leu Gln Ile Thr Cys Ser Ile
        675                 680                 685

Ser His Gln Val Glu Ala Lys Lys Asp Glu Ser Trp Gln Gly Thr Val
    690                 695                 700

Thr Asp Thr Arg Met Ser Asp Glu Ile Val His Asn Leu Asp Gly Cys
705                 710                 715                 720

Glu Ile Ser Leu Val Gly Asp Asp Leu Asp Pro Glu Arg Glu Ser Leu
                725                 730                 735

Leu Leu Asp Thr Thr Ser Leu Gln Gln Arg Gly Leu Glu Leu Thr Asn
            740                 745                 750

Thr Ser Ala Tyr Leu Thr Ile Ala Gly Val Glu Ser Ile Thr Val Tyr
        755                 760                 765

Glu Glu Ile Leu Arg Gln Ala Arg Tyr Arg Leu Arg His Gly Ala Ala
    770                 775                 780

Leu Tyr Thr Arg Lys Phe Arg Leu Ser Cys Ser Glu Met Asn Gly Arg
785                 790                 795                 800

Tyr Ser Ser Asn Glu Phe Ile Val Glu Val Asn Val Leu His Ser Met
                805                 810                 815

Asn Arg Val Ala His Pro Ser His Val Leu Ser Ser Gln Gln Phe Leu
            820                 825                 830

His Arg Gly His Gln Pro Pro Glu Met Ala Gly His Ser Leu Ala
        835                 840                 845

Ser Ser His Arg Asn Ser Met Ile Pro Ser Ala Ala Thr Leu Ile Ile
    850                 855                 860

Val Val Cys Val Gly Phe Leu Leu Met Val Val Leu Gly Leu Val
865                 870                 875                 880

Arg Ile His Ser Leu His Arg Arg Val Ser Gly Ala Gly Pro Pro
                885                 890                 895

Gly Ala Ser Ser Asp Pro Lys Asp Pro Asp Leu Phe Trp Asp Asp Ser
            900                 905                 910
```

```
Ala Leu Thr Ile Ile Val Asn Pro Met Glu Ser Tyr Gln Asn Arg Gln
        915                 920                 925

Ser Cys Val Thr Gly Ala Val Gly Gly Gln Gln Glu Asp Glu Asp Ser
        930                 935                 940

Ser Asp Ser Glu Val Ala Asp Ser Pro Ser Ser Asp Glu Arg Arg Ile
945                 950                 955                 960

Ile Glu Thr Pro Pro His Arg Tyr
                965

<210> SEQ ID NO 3
<211> LENGTH: 955
<212> TYPE: PRT
<213> ORGANISM: human

<400> SEQUENCE: 3

Met Leu Pro Gly Arg Leu Cys Trp Val Pro Leu Leu Leu Ala Leu Gly
1               5                   10                  15

Val Gly Ser Gly Ser Gly Gly Gly Asp Ser Arg Gln Arg Arg Leu
                20                  25                  30

Leu Ala Ala Lys Val Asn Lys His Lys Pro Trp Ile Glu Thr Ser Tyr
            35                  40                  45

His Gly Val Ile Thr Glu Asn Asn Asp Thr Val Ile Leu Asp Pro Pro
        50                  55                  60

Leu Val Ala Leu Asp Lys Asp Ala Pro Val Pro Phe Ala Gly Glu Ile
65                  70                  75                  80

Cys Ala Phe Lys Ile His Gly Gln Glu Leu Pro Phe Glu Ala Val Val
                85                  90                  95

Leu Asn Lys Thr Ser Gly Glu Gly Arg Leu Arg Ala Lys Ser Pro Ile
            100                 105                 110

Asp Cys Glu Leu Gln Lys Glu Tyr Thr Phe Ile Ile Gln Ala Tyr Asp
        115                 120                 125

Cys Gly Ala Gly Pro His Glu Thr Ala Trp Lys Lys Ser His Lys Ala
    130                 135                 140

Val Val His Ile Gln Val Lys Asp Val Asn Glu Phe Ala Pro Thr Phe
145                 150                 155                 160

Lys Glu Pro Ala Tyr Lys Ala Val Val Thr Glu Gly Lys Ile Tyr Asp
                165                 170                 175

Ser Ile Leu Gln Val Glu Ala Ile Asp Glu Asp Cys Ser Pro Gln Tyr
            180                 185                 190

Ser Gln Ile Cys Asn Tyr Glu Ile Val Thr Thr Asp Val Pro Phe Ala
        195                 200                 205

Ile Asp Arg Asn Gly Asn Ile Arg Asn Thr Glu Lys Leu Ser Tyr Asp
    210                 215                 220

Lys Gln His Gln Tyr Glu Ile Leu Val Thr Ala Tyr Asp Cys Gly Gln
225                 230                 235                 240

Lys Pro Ala Ala Gln Asp Thr Leu Val Gln Val Asp Val Lys Pro Val
                245                 250                 255

Cys Lys Pro Gly Trp Gln Asp Trp Thr Lys Arg Ile Glu Tyr Gln Pro
            260                 265                 270

Gly Ser Gly Ser Met Pro Leu Phe Pro Ser Ile His Leu Glu Thr Cys
        275                 280                 285

Asp Gly Ala Val Ser Ser Leu Gln Ile Val Thr Glu Leu Gln Thr Asn
    290                 295                 300

Tyr Ile Gly Lys Gly Cys Asp Arg Glu Thr Tyr Ser Glu Lys Ser Leu
305                 310                 315                 320
```

-continued

```
Gln Lys Leu Cys Gly Ala Ser Ser Gly Ile Ile Asp Leu Leu Pro Ser
            325                 330                 335

Pro Ser Ala Ala Thr Asn Trp Thr Ala Gly Leu Leu Val Asp Ser Ser
                340                 345                 350

Glu Met Ile Phe Lys Phe Asp Gly Arg Gln Gly Ala Lys Ile Pro Asp
            355                 360                 365

Gly Ile Val Pro Lys Asn Leu Thr Asp Gln Phe Thr Ile Thr Met Trp
        370                 375                 380

Met Lys His Gly Pro Ser Pro Gly Val Arg Ala Glu Lys Glu Thr Ile
385                 390                 395                 400

Leu Cys Asn Ser Asp Lys Thr Glu Met Asn Arg His His Tyr Ala Leu
                405                 410                 415

Tyr Val His Asn Cys Arg Leu Val Phe Leu Leu Arg Lys Asp Phe Asp
                420                 425                 430

Gln Ala Asp Thr Phe Arg Pro Ala Glu Phe His Trp Lys Leu Asp Gln
            435                 440                 445

Ile Cys Asp Lys Glu Trp His Tyr Tyr Val Ile Asn Val Glu Phe Pro
        450                 455                 460

Val Val Thr Leu Tyr Met Asp Gly Ala Thr Tyr Glu Pro Tyr Leu Val
465                 470                 475                 480

Thr Asn Asp Trp Pro Ile His Pro Ser His Ile Ala Met Gln Leu Thr
                485                 490                 495

Val Gly Ala Cys Trp Gln Gly Gly Glu Val Thr Lys Pro Gln Phe Ala
                500                 505                 510

Gln Phe Phe His Gly Ser Leu Ala Ser Leu Thr Ile Arg Pro Gly Lys
            515                 520                 525

Met Glu Ser Gln Lys Val Ile Ser Cys Leu Gln Ala Cys Lys Glu Gly
            530                 535                 540

Leu Asp Ile Asn Ser Leu Glu Ser Leu Gly Gln Gly Ile Lys Tyr His
545                 550                 555                 560

Phe Asn Pro Ser Gln Ser Ile Leu Val Met Glu Gly Asp Asp Ile Gly
                565                 570                 575

Asn Ile Asn Arg Ala Leu Gln Lys Val Ser Tyr Ile Asn Ser Arg Gln
            580                 585                 590

Phe Pro Thr Ala Gly Val Arg Arg Leu Lys Val Ser Ser Lys Val Gln
            595                 600                 605

Cys Phe Gly Glu Asp Val Cys Ile Ser Ile Pro Glu Val Asp Ala Tyr
        610                 615                 620

Val Met Val Leu Gln Ala Ile Glu Pro Arg Ile Thr Leu Arg Gly Thr
625                 630                 635                 640

Asp His Phe Trp Arg Pro Ala Ala Gln Phe Glu Ser Ala Arg Gly Val
                645                 650                 655

Thr Leu Phe Pro Asp Ile Lys Ile Val Ser Thr Phe Ala Lys Thr Glu
                660                 665                 670

Ala Pro Gly Asp Val Lys Thr Thr Asp Pro Lys Ser Glu Val Leu Glu
            675                 680                 685

Glu Met Leu His Asn Leu Asp Phe Cys Asp Ile Leu Val Ile Gly Gly
            690                 695                 700

Asp Leu Asp Pro Arg Gln Glu Cys Leu Glu Leu Asn His Ser Glu Leu
705                 710                 715                 720

His Gln Arg His Leu Asp Ala Thr Asn Ser Thr Ala Gly Tyr Ser Ile
                725                 730                 735
```

```
Tyr Gly Val Gly Ser Met Ser Arg Tyr Glu Gln Val Leu His His Ile
            740                 745                 750
Arg Tyr Arg Asn Trp Arg Pro Ala Ser Leu Glu Ala Arg Arg Phe Arg
        755                 760                 765
Ile Lys Cys Ser Glu Leu Asn Gly Arg Tyr Thr Ser Asn Glu Phe Asn
770                 775                 780
Leu Glu Val Ser Ile Leu His Glu Asp Gln Val Ser Asp Lys Glu His
785                 790                 795                 800
Val Asn His Leu Ile Val Gln Pro Pro Phe Leu Gln Ser Val His His
                805                 810                 815
Pro Glu Ser Arg Ser Ser Ile Gln His Ser Ser Val Val Pro Ser Ile
            820                 825                 830
Ala Thr Val Val Ile Ile Ile Ser Val Cys Met Leu Val Phe Val Val
        835                 840                 845
Ala Met Gly Val Tyr Arg Val Arg Ile Ala His Gln His Phe Ile Gln
    850                 855                 860
Glu Thr Glu Ala Ala Lys Glu Ser Glu Met Asp Trp Asp Asp Ser Ala
865                 870                 875                 880
Leu Thr Ile Thr Val Asn Pro Met Glu Lys His Glu Gly Pro Gly His
                885                 890                 895
Gly Glu Asp Glu Thr Glu Gly Glu Glu Glu Ala Glu Glu Glu
            900                 905                 910
Met Ser Ser Ser Ser Gly Ser Asp Asp Ser Glu Glu Glu Glu Glu Glu
        915                 920                 925
Glu Gly Met Gly Arg Gly Arg His Gly Gln Asn Gly Ala Arg Gln Ala
    930                 935                 940
Gln Leu Glu Trp Asp Asp Ser Thr Leu Pro Tyr
945                 950                 955

<210> SEQ ID NO 4
<211> LENGTH: 27
<212> TYPE: PRT
<213> ORGANISM: human

<400> SEQUENCE: 4

Ala Ala Gln Pro Gln Phe Val His Pro Glu His Arg Ser Phe Val Asp
1               5                   10                  15
Leu Ser Gly His Asn Leu Ala Asn Pro His Pro
            20                  25

<210> SEQ ID NO 5
<211> LENGTH: 28
<212> TYPE: PRT
<213> ORGANISM: human

<400> SEQUENCE: 5

Ala Ala Gln Pro Gln Phe Val His Pro Glu His Arg Ser Phe Val Asp
1               5                   10                  15
Leu Ser Gly His Asn Leu Ala Asn Pro His Pro Phe
            20                  25

<210> SEQ ID NO 6
<211> LENGTH: 36
<212> TYPE: PRT
<213> ORGANISM: human
```

```
<400> SEQUENCE: 6

Ala Ala Gln Pro Gln Phe Val His Pro Glu His Arg Ser Phe Val Asp
1               5                   10                  15

Leu Ser Gly His Asn Leu Ala Asn Pro His Pro Phe Ala Val Val Pro
            20                  25                  30

Ser Thr Ala Thr
        35

<210> SEQ ID NO 7
<211> LENGTH: 22
<212> TYPE: PRT
<213> ORGANISM: human

<400> SEQUENCE: 7

Phe Val His Pro Glu His Arg Ser Phe Val Asp Leu Ser Gly His Asn
1               5                   10                  15

Leu Ala Asn Pro His Pro
            20

<210> SEQ ID NO 8
<211> LENGTH: 23
<212> TYPE: PRT
<213> ORGANISM: human

<400> SEQUENCE: 8

Phe Val His Pro Glu His Arg Ser Phe Val Asp Leu Ser Gly His Asn
1               5                   10                  15

Leu Ala Asn Pro His Pro Phe
            20

<210> SEQ ID NO 9
<211> LENGTH: 31
<212> TYPE: PRT
<213> ORGANISM: human

<400> SEQUENCE: 9

Phe Val His Pro Glu His Arg Ser Phe Val Asp Leu Ser Gly His Asn
1               5                   10                  15

Leu Ala Asn Pro His Pro Phe Ala Val Val Pro Ser Thr Ala Thr
            20                  25                  30

<210> SEQ ID NO 10
<211> LENGTH: 4
<212> TYPE: PRT
<213> ORGANISM: human

<400> SEQUENCE: 10

Asn Pro His Pro
1

<210> SEQ ID NO 11
<211> LENGTH: 5
<212> TYPE: PRT
<213> ORGANISM: human

<400> SEQUENCE: 11

Asn Pro His Pro Phe
1               5
```

```
<210> SEQ ID NO 12
<211> LENGTH: 13
<212> TYPE: PRT
<213> ORGANISM: human

<400> SEQUENCE: 12

Asn Pro His Pro Phe Ala Val Val Pro Ser Thr Ala Thr
1               5                   10

<210> SEQ ID NO 13
<211> LENGTH: 73
<212> TYPE: PRT
<213> ORGANISM: Human

<400> SEQUENCE: 13

Ile Ser Glu Val Lys Met Asp Ala Glu Phe Arg His Asp Ser Gly Tyr
1               5                   10                  15

Glu Val His His Gln Lys Leu Val Phe Phe Ala Glu Asp Val Gly Ser
            20                  25                  30

Asn Lys Gly Ala Ile Ile Gly Leu Met Val Gly Gly Val Val Ile Ala
        35                  40                  45

Thr Val Ile Val Ile Thr Leu Val Met Leu Lys Lys Lys Gln Tyr Thr
    50                  55                  60

Ser Ile His His Gly Val Val Gln Asn
65                  70

<210> SEQ ID NO 14
<211> LENGTH: 37
<212> TYPE: PRT
<213> ORGANISM: Human

<400> SEQUENCE: 14

Ala Ala Gln Pro Gln Phe Val His Pro Glu His Arg Ser Phe Val Asp
1               5                   10                  15

Leu Ser Gly His Asn Leu Ala Asn Pro His Pro Phe Ala Val Val Pro
            20                  25                  30

Ser Thr Ala Thr Val
        35

<210> SEQ ID NO 15
<211> LENGTH: 38
<212> TYPE: PRT
<213> ORGANISM: Human

<400> SEQUENCE: 15

Ala Ala Gln Pro Gln Phe Val His Pro Glu His Arg Ser Phe Val Asp
1               5                   10                  15

Leu Ser Gly His Asn Leu Ala Asn Pro His Pro Phe Ala Val Val Pro
            20                  25                  30

Ser Thr Ala Thr Val Val
        35

<210> SEQ ID NO 16
<211> LENGTH: 39
<212> TYPE: PRT
<213> ORGANISM: Human
```

```
<400> SEQUENCE: 16

Ala Ala Gln Pro Gln Phe Val His Pro Glu His Arg Ser Phe Val Asp
1               5                   10                  15

Leu Ser Gly His Asn Leu Ala Asn Pro His Pro Phe Ala Val Val Pro
                20                  25                  30

Ser Thr Ala Thr Val Val Ile
        35

<210> SEQ ID NO 17
<211> LENGTH: 40
<212> TYPE: PRT
<213> ORGANISM: Human

<400> SEQUENCE: 17

Ala Ala Gln Pro Gln Phe Val His Pro Glu His Arg Ser Phe Val Asp
1               5                   10                  15

Leu Ser Gly His Asn Leu Ala Asn Pro His Pro Phe Ala Val Val Pro
                20                  25                  30

Ser Thr Ala Thr Val Val Ile Val
        35                  40
```